US012685704B2

(12) United States Patent
Sinha et al.

(10) Patent No.: US 12,685,704 B2
(45) Date of Patent: Jul. 21, 2026

(54) MULTIPHASE CLEANSING COMPOSITION

(71) Applicant: L'OREAL, Paris (FR)

(72) Inventors: Ritesh Kumar Sinha, Linden, NJ (US); Hy Si Bui, Piscataway, NJ (US); Xuefei Liu, Edison, NJ (US)

(73) Assignee: L'OREAL, Paris (FR)

(*) Notice: Subject to any disclaimer, the term of this patent is extended or adjusted under 35 U.S.C. 154(b) by 384 days.

(21) Appl. No.: 18/543,728

(22) Filed: Dec. 18, 2023

(65) Prior Publication Data

US 2025/0195392 A1 Jun. 19, 2025

(51) Int. Cl.

| | |
|---|---|
| ***A61Q 1/00*** | (2006.01) |
| ***A61K 8/19*** | (2006.01) |
| ***A61K 8/31*** | (2006.01) |
| ***A61K 8/34*** | (2006.01) |
| ***A61K 8/37*** | (2006.01) |
| ***A61K 8/81*** | (2006.01) |
| ***A61K 8/92*** | (2006.01) |
| ***A61Q 1/14*** | (2006.01) |
| ***A61Q 5/02*** | (2006.01) |
| ***A61Q 19/10*** | (2006.01) |

(52) U.S. Cl.

CPC .............. *A61K 8/8152* (2013.01); *A61K 8/19* (2013.01); *A61K 8/31* (2013.01); *A61K 8/345* (2013.01); *A61K 8/37* (2013.01); *A61K 8/922* (2013.01); *A61Q 1/14* (2013.01); *A61Q 5/02* (2013.01); *A61Q 19/10* (2013.01)

(58) Field of Classification Search

CPC .......... A61K 8/8152; A61K 8/19; A61K 8/31; A61K 8/345; A61K 8/37; A61K 8/922; A61K 8/03; A61K 8/34; A61Q 1/14; A61Q 5/02; A61Q 19/10

USPC .......................................................... 510/119

See application file for complete search history.

(56) References Cited

U.S. PATENT DOCUMENTS

| | | | | |
|---|---|---|---|---|
| 5,437,793 A | | 8/1995 | Alper | |
| 5,698,139 A | * | 12/1997 | Alper | B01D 17/047 210/733 |
| 5,837,146 A | | 11/1998 | Alper | |
| 5,961,823 A | | 10/1999 | Alper | |
| 6,180,010 B1 | | 1/2001 | Alper | |

(Continued)

FOREIGN PATENT DOCUMENTS

| | | | | |
|---|---|---|---|---|
| FR | 2864893 A1 | | 7/2005 | |
| FR | 3007638 A1 | | 1/2015 | |
| WO | WO 2008127861 A2 | * | 10/2008 | A61Q 19/10 |

OTHER PUBLICATIONS

Preliminary Search Report and Written Opinion issued on Aug. 19, 2024 for corresponding French Application No. FR 2401844.

*Primary Examiner* — Eisa B Elhilo

(74) *Attorney, Agent, or Firm* — POLSINELLI PC

(57) ABSTRACT

A multiphase cleansing composition is disclosed, useful for cleansing the skin or hair, for example, for removing makeup from the skin or hair. The multiphase cleansing composition comprises an oil phase and an aqueous phase. The oil phase comprises: (a) a hydrophobic polymer formed as a reaction product of a natural or food-derived oil and a methacrylate or acrylate polymer; (b) one or more solvents capable of solubilizing the hydrophobic polymer of (a). The aqueous phase comprises water and optionally one or more water soluble solvents and one or more electrolytes. Methods of cleansing skin and hair are also described.

17 Claims, 2 Drawing Sheets

Immediately After Shaking

D (Comparative) A B C

(56) References Cited

U.S. PATENT DOCUMENTS

| | | | | |
|---|---|---|---|---|
| 6,337,016 | B1 | 1/2002 | Alper | |
| 6,475,393 | B2 | 11/2002 | Alper | |
| 6,491,822 | B2 | 12/2002 | Alper | |
| 6,805,727 | B2 | 10/2004 | Alper | |
| 7,264,721 | B2 | 9/2007 | Alper | |
| 2008/0242573 | A1 * | 10/2008 | Wei | A61K 8/03 510/159 |
| 2011/0309022 | A1 | 12/2011 | Briggs et al. | |
| 2012/0316251 | A1 | 12/2012 | Alper | |
| 2015/0305330 | A1 | 10/2015 | Alper | |
| 2019/0232195 | A1 | 8/2019 | Alper | |
| 2021/0401706 | A1 | 12/2021 | Uehara Matsuoka | |
| 2022/0249342 | A1 * | 8/2022 | Mitra | A61Q 1/14 |
| 2023/0057412 | A1 | 2/2023 | Foley et al. | |
| 2023/0058226 | A1 | 2/2023 | Foley et al. | |
| 2023/0063141 | A1 | 3/2023 | Foley et al. | |
| 2023/0089419 | A1 | 3/2023 | Gupta et al. | |
| 2023/0190601 | A1 | 6/2023 | Gupta et al. | |
| 2023/0285254 | A1 | 9/2023 | Braganza | |
| 2023/0346684 | A1 | 11/2023 | Piccirillo et al. | |
| 2023/0382776 | A1 | 11/2023 | Alper | |
| 2025/0195399 | A1 * | 6/2025 | Sinha | A61K 8/046 |

* cited by examiner

Immediately After Shaking

D (Comparative) A B C

15 Seconds After Shaking

D (Comparative) A B C

25 Seconds After shaking

MULTIPHASE CLEANSING COMPOSITION

FIELD OF THE DISCLOSURE

The instant disclosure is drawn to multiphase cleansing compositions comprising a hydrophobic polymer resulting from a reaction product of a natural or food-derived oil and a methacrylate or acrylate polymer. Methods for making and using the multiphase cleansing compositions are also described.

BACKGROUND

Personal cleansing products have traditionally been marketed in a variety of forms such as bar soaps, creams, lotions, and gels. These cleansing products seek to satisfy multiple criteria to be acceptable to consumers. For example, a cleansing product should exhibit good cleansing properties, be easily applied, and mild to the skin while preferably providing moisturization. Ideal personal cleansers should gently cleanse the skin or hair, cause little or no irritation, and not leave the skin or hair overly dry after frequent use.

Consumers regularly cleanse skin and hair using a single type of composition intended to remove dirt, oil, and makeup. It is difficult, however, to remove all types of debris from the skin and hair with a single product because many products do not adequately remove both oily material and water-soluble material simultaneously Therefore, consumers sometimes engage in "double cleansing" to remove all types of unwanted debris from the skin and hair. Double cleansing involves initially cleansing the skin with an oil-based cleanser to solubilize oils, sunscreen, and other lipophilic material that is present on skin, including makeup. Subsequently, a water-based cleanser is employed to wash away dirt, sweat, and salts. The theory is that washing first with an oil-based cleanser, followed by a water-based one, will thoroughly eliminate all types of substances on the skin and thereby providing complete cleansing.

Compositions having both aqueous and fatty phases have been formulated as emulsions. Common cleansing emulsions can be water-based, with an oil phase suspended as droplets throughout an aqueous phase. Unlike moisturizers, which tend to have a thicker and creamier consistency, emulsions can be thin, fluid, and often have a milky appearance. Cleansing emulsions attempt to provide the cleansing properties of both the water-phase and oil-phase simultaneously. However, ensuring stability of emulsions requires the use of emulsifiers, which form an interface between the oil droplets and the water phase that suspend the oil droplets throughout the aqueous phase. Such compositions also often include cleansing surfactants, which tend to unnecessarily dry the skin. Therefore, it would be beneficial to have a single cleansing product containing multiple phases, such as an aqueous phase and one or more oil phases, that effectively cleanses skin and hair without requiring emulsifiers or cleansing surfactants.

SUMMARY OF THE DISCLOSURE

Multiphase cleansing compositions useful for cleansing the skin and hair are described. When agitated, the multiphase cleansing composition forms a single application phase but when left standing, the composition rapidly phase separates into at least two visibly distinct phases, at least one oil phase and an aqueous phase. The multiphase cleansing composition provides an esthetically interesting and useful cleansing composition that is very effective for cleansing skin and hair. The composition is particularly useful for removing makeup, pollution, or debris in a single treatment. The oil phase solubilizes and helps remove fatty material from the skin and hair, such as oils, sebum, and lipophilic cosmetic ingredients. The aqueous phase, on the other hand, solubilizes and removes salts and water-soluble material, provides hydration, and assists with removing makeup or other debris from the skin and hair when rinsing the cleansing composition from the skin or hair.

The multiphase cleansing composition includes:

(i) an oil phase comprising:
- (a) a hydrophobic polymer formed as a reaction product of a natural or food-derived oil and a methacrylate or acrylate polymer;
- (b) one or more solvents capable of solubilizing the reaction product of (i)(a);

(ii) an aqueous phase comprising:
- (ii)(a) water.

The hydrophobic polymer is a reaction product of a natural or food-derived oil and an acrylate or methacrylate polymer. According to further embodiments, the hydrophobic polymer is a reaction product of a natural or food-derived oil and a methacrylate polymer. The natural or food-derived oil may be a drying oil or a semi-drying oil. Nonlimiting examples include linseed oil, sunflower oil, tung oil, fish oil, cottonseed oil, soybean oil, or combinations thereof. The methacrylate polymer can be formed from methacrylate monomers, for example, monomers selected from isobutyl methacrylate, methyl methacrylate, ethyl methacrylate, n-butyl methacrylate, and combinations thereof. In a preferred embodiment, the hydrophobic polymer is formed from a natural or food-derived oil and an isobutyl methacrylate polymer and may preferably be an isobutyl methacrylate polymer.

In various embodiments, the hydrophobic polymer is the reaction product of about 50 to about 85 parts by weight of the natural or food-derived oil and about 15 to about 50 parts by weight of the methacrylate or acrylate polymer. More specifically, the hydrophobic polymer may be the reaction product of about 72 to about 77 parts by weight of the natural or food-derived oil and about 23 to about 28 parts by weight of a methacrylate polymer. For example, the hydrophobic polymer may be the reaction product of linseed oil and poly(isobutyl methacrylate) in a suitable solvent, such as, for example, 2,2,4-trimethyl-1,3-pentanediol monoisobutyrate. Preferably, the reaction product is formed from about 72 to about 77% of linseed oil and about 23 to about 28% of isobutyl methacrylate polymer in a suitable solvent, such as 2,2,4-trimethyl-1,3-pentanediol monoisobutyrate.

One or more solvents capable of solubilizing the hydrophobic polymer of (i)(a) are used to solubilize the hydrophobic polymer. A single solvent may be used or a combination of solvents, wherein the combination of solvents is capable of solubilizing the hydrophobic polymer. In various embodiments, the one or more solvents capable of solubilizing the reaction product of (a) have a dispersion component (D), a polar component (P), a hydrogen bonding component (H), and a distance (Ra) per Hansen Solubility Parameter of less than or equal to 13.4 $MPa^{0.5}$, wherein the distance (Ra) is defined by formula (I):

$$Ra = \sqrt{4(D - D_1)^2 + (P - P_1)^2 + (H - H_1)^2} \quad (I)$$

wherein $D_1$ is 16.8 $MPa^{0.5}$, $P_1$ is 4.8 $MPa^{0.5}$, and $H_1$ is 13.0 $MPa^{0.5}$.

Nonlimiting examples of solvents capable of solubilizing the hydrophobic polymer of (i)(a) include polycitronellol acetate, caprylic/capric triglyceride, isododecane, isohexadecane, tetradecane, isopropyl myristate, isopropyl alcohol, octyldodecanol, ethanol, phenoxyethanol, castor oil, and mixtures thereof. Polycitronellol acetate is particularly useful.

The aqueous phase of the multiphase cleansing composition includes a significant proportion of water or may consist of water. The aqueous phase optionally may include one or more water soluble solvents, one or more electrolytes, or combinations thereof. Nonlimiting examples of water soluble solvents include $C_2$-$C_6$ mono-alcohols (e.g., ethanol, isopropyl alcohol, etc.), polyols (polyhydric alcohols), glycols (e.g., ethylene glycol, propylene glycol, butylene glycol, pentylene glycol, caprylyl glycol, etc.), and mixtures thereof.

Nonlimiting examples of electrolytes include sodium chloride, ammonium chloride, magnesium chloride, sodium sulfate, sodium citrate, or combinations thereof.

In various embodiments, the multiphase cleansing composition is free or essentially free of emulsifiers and surfactants. Nonetheless, in other embodiments, one or more emulsifiers and surfactants may optionally be included in the multiphase cleansing composition.

The multiphase cleansing composition typically phase separates shortly after the multiple phases are mixed, for example, by shaking. The multiphase cleansing composition may phase separate forming two distinct phases with a single interface with 15 minutes after shaking at about 25° C. In further embodiments, the multiphase cleansing composition will visibly phase separate into two or more layers within about 10 minutes, 8 minutes, 5 minutes, or 2 minutes after shaking at 25° C.

The instant disclosure is further drawn to methods for cleansing skin or hair using the multiphase cleansing composition. For example, methods for cleansing the skin or hair typically comprise initially shaking or mixing the multiphase cleansing composition so that the multiple phases are temporarily combined for application to the skin or hair. When the multiple phases are temporarily combined, the composition may be referred to as a "mixed application composition." After the multiple phases are temporarily combined, for example, by shaking, the mixed application composition may be applied to the skin or hair to penetrate and dislodge dirt, makeup, pollution, or other contaminates to be cleansed from the skin or hair. The skin or hair upon which the multiphase cleansing composition (the mixed application composition) is applied can be removed by wiping with a wipe, cloth, hand, or other substrate and/or can be rinsed from the skin or hair, thereby cleansing the skin or hair.

In further embodiments, the multiphase cleansing composition is preferably used in methods for removing makeup from the skin or hair, preferably from the skin. After shaking or mixing the multiphase cleansing composition to form a mixed application composition, the mixed application composition is applied to skin or hair upon which makeup is present. The various ingredients of the multiphase cleansing composition can penetrate, dislodge, or solubilize the makeup such that the makeup is easily wiped or rinsed from the skin or hair.

BRIEF DESCRIPTION OF THE DRAWINGS

Implementation of the present technology is described, by way of example only, with reference to the attached figures, wherein:

FIG. 1(*b*) shows a comparative composition and inventive compositions 15 seconds after mixing.

FIG. 1(*c*) shows a comparative composition and inventive compositions 25 seconds after mixing.

Figure 1A:
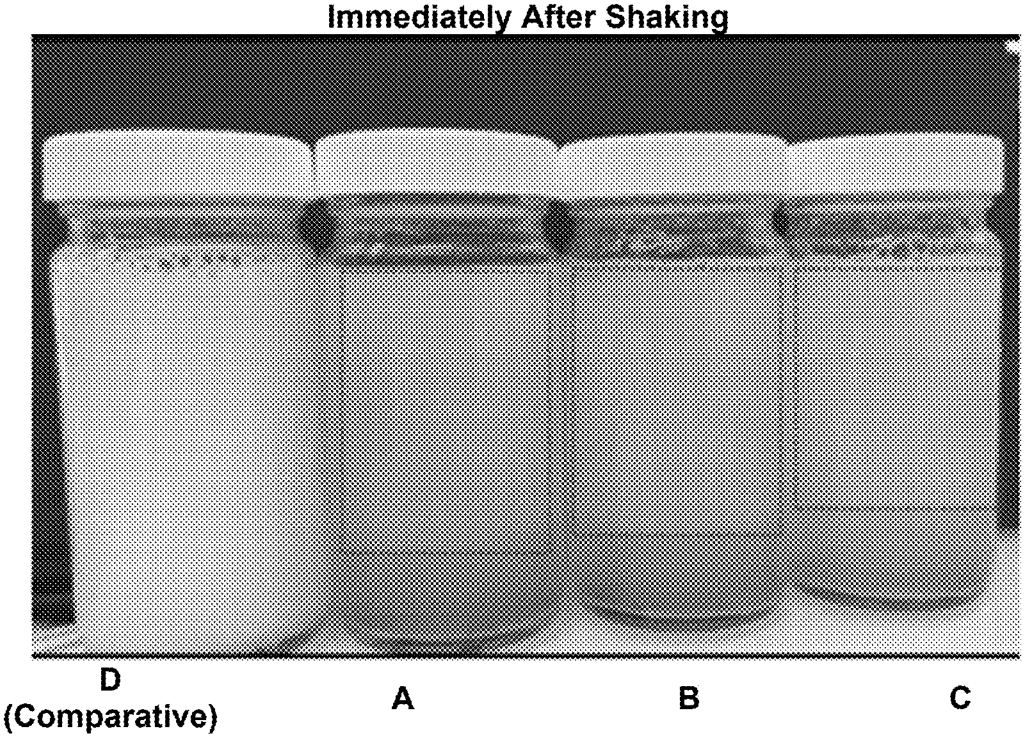
FIG. 1(*a*) shows a comparative composition and inventive compositions immediately after mixing.

The various aspects of the invention are not limited to the arrangements and instrumentality shown in the drawings.

DETAILED DESCRIPTION OF THE DISCLOSURE

By the term "multiphase" or "multi-phase" as used herein, is meant that the phases of the compositions occupy separate but visually distinct physical spaces inside the package in which they are stored, but are in direct contact with one another (i.e., they are not separated by a barrier, and they are not emulsified or mixed to any significant degree). In a preferred embodiment, the "multiphase" cleansing compositions comprise two visually distinct phases which are present within the container as a visually distinct pattern. Preferably, the two visually distinct phases form a single interface between one another, i.e., the two phases separate from one another (phase separate).

The multiphase cleansing compositions include an oil phase and an aqueous phase. The oil phase includes:

(a) a hydrophobic polymer formed as a reaction product of a natural or food-derived oil and a methacrylate or acrylate polymer; and (b) one or more solvents capable of solubilizing the hydrophobic polymer (i)(a).

The aqueous phase includes primarily water and may be exclusively water. However, in certain embodiments, the aqueous phase includes:

(a) water;

(b) one or more water soluble solvents; and (c) one or more electrolytes.

The weight ratio of the oil phase to the aqueous phase will vary. In certain embodiments, however, the oil phase and the aqueous phase are in a weight ratio of about 1:3 to about 3:1. In further embodiments, the weight ratio of the oil phase to the aqueous phase is from about 1:2 to about 2:1, about 1:1.5 to about 1.5:1, or about 1:1.

The multiple phases of the multiphase cleansing composition can be temporarily mixed, for example, by shaking or by mixing the phases together. However, the multiphase cleansing composition does not remain mixed and will eventually phase separate. The multiphase composition is typically mixed or shaken immediately before use to temporarily mix the multiple phases together. The temporarily mixed multiphase composition may be referred to an "application composition" because the mixture is used for application to the skin or hair.

After mixing the multiple phases together, the mixture (the application composition) will eventually phase separate, preferably into two or more visually distinct phases. For example, two visually distinct phases can form having a single interface. In certain embodiments, the multiphase cleansing composition will phase separate within about 15 minutes at rest after shaking by hand, at a temperature of about 25° C. In further embodiments, the multiphase cleansing composition will phase separate, after mixing the multiphase composition by shaking by hand, within about 12 minutes, within about 10 minutes, within about 8 minutes, within about 5 minutes, within about 3 minutes, or within about 1 minute. In other embodiments, it may be preferable for the multiphase cleansing composition to take longer to phase separate. For example, the multiphase cleansing composition may phase separate in about 1 minute to about 8 hours at rest after shaking by hand. In further embodiments, the multiphase cleansing composition may phase separate in about 5 minutes to about 8 hours, in about 10 minutes to about 8 hours, in about 30 minutes to about 8 hours, in about 1 hour to about 8 hours, in about 2 hours to about 8 hours, or in about 4 hours to about 8 hours.

(a) Hydrophobic Polymer

The hydrophobic polymer is a reaction product of a natural or food-derived oil (oil component) and an acrylate component. In particular, the natural or food-derived oil may be a drying oil, preferably linseed oil. The reaction product may include an isobutyl methacrylate backbone with a plurality of linseed oil side chains. Preferably, the reaction product is a product sold under the MYCELX® brand from MYCELX Technologies Corporation of Gainesville, Georgia. See U.S. Pat. No. 5,698,139 for a description of MYCELX materials, which is incorporated herein by reference in its entirety.

The hydrophobic polymer is comprised of an oil component and a polymer component, typically reacted in a solvent. In a preferred embodiment, the hydrophobic polymer is a reaction product of linseed oil and poly(isobutyl methacrylate) in a solvent such as 2,2,4-trimethyl-1,3-pentanediol-monoisobutyrate as a solvent. The oil component is derived from glycerin and carboxylic acids, such as linseed fatty acid to form monoglycerides, diglycerides, and triglycerides. The oil component is preferably derived from plant/vegetable or natural origin. Vegetable oils are obtained by cold pressing the seeds of a plant to obtain the oil contained therein. Of the vegetable oils, drying oils such as linseed and tung oil, semi-drying oils such as soybean and cotton seed oil, and non-drying oils such as coconut oil may be used as the oil component. The oil component typically forms about 72% to 77%, or most preferably, 74.62%, of the hydrophobic polymer (e.g., linseed oil/isobutyl methacrylate).

The polymer component may be derived from α and β-unsaturated carbonyl compounds. The polymer component is the resultant product of a monomer which is an ester of an acrylic acid, crotonic acid, isocrotonic acid, methacrylic acid, sorbic acid, cinnamic acid, maleic acid, fumaric acid, and methyl methacrylic acid. Nonlimiting examples of useful polymers which cover any number of reaction possibilities between the esters of such compounds include acrylate polymers, methyl methacrylate polymers, methyl/n-butyl methacrylate polymers, methacrylate copolymers, ethyl methacrylate, n-butyl methacrylate, isobutyl methacrylate, n-butyl/isobutyl methacrylate copolymers, or combinations thereof.

Preferably the polymer is poly(isobutyl methacrylate). In particular, the polymer percentage may be from about 23% to about 28%, or about 25.28%, of the hydrophobic polyer, e.g., poly(linseed oil/isobutyl methacrylate). The hydrophobic polymer is a reaction product typically formed in a liquid solvent able to dissolve or dilute the polymer component (poly(oil/polymer)) and the hydrophobic polymer. The solvent, or diluent should generally comprise any liquid or mixture of liquids that is able to dissolve or dilute hydrophobic polymer product. The solvent/diluent can control the evaporation, desired flow, and coalescing of the hydrophobic polymer. The solvent may be, for example, an aliphatic hydrocarbon, aromatic hydrocarbon, alcohols, ketones, ethers, aldehydes, phenols, carboxylic acids, carboxylates, synthetic chemicals and naturally occurring substances. Preferably the solvent is 2,2,4-trimethyl-1,3-pentanediol-monoisobutyrate. Hydrophobic polymers according to the instant disclosure and methods for making them are described, for example, in U.S. Pat. Nos. 5,437,793, 5,698,139, 5,837,146, 5,961,823, 6,180,010, 6,475,393, and 6,805,727, which are incorporated herein by reference in their entireties. The preferred hydrophobic polymer may be designated as poly(linseed oil/isobutyl methacrylate).

The amount of hydrophobic polymer in the oil phase will vary. Nonetheless, the total amount of the hydrophobic polymer is typically from about 0.01 to about 4 wt. %, based on the total weight of the oil phase. In further embodiment, the total amount of the hydrophobic polymer is from about 0.01 to about 3 wt. %, about 0.01 to about 2.5 wt. % about 0.01 to about 2 wt. %, 0.01 to about 1.8 wt. %, about 0.01 to about 1.5 wt. %, about 0.01 to about 1.2 wt. %, about 0.01 to about 1 wt. %, about 0.01 to about 0.8 wt. %, about 0.01 to about 0.5 wt. %, about 0.02 to about 4 wt. %, about 0.02 to about 3 wt. %, about 0.02 to about 2.5 wt. %, about 0.02 to about 2 wt. %, about 0.02 to about 1.8 wt. %, about 0.02 to about 1.5 wt. %, about 0.02 to about 1.2 wt. %, about 0.02 to about 1 wt. %, about 0.02 to about 0.8 wt. %, about 0.02 to about 0.5 wt. %, about 0.05 to about 4 wt. %, about 0.05 to about 3 wt. %, about 0.05 to about 2.5 wt. %, about 0.05 to about 2 wt. %, about 0.05 to about 1.8 wt. %, about 0.05 to about 1.5 wt. %, about 0.05 to about 1.2 wt. %, about 0.05 to about 1 wt. %, about 0.05 to about 0.8 wt. %, about 0.05 to about 0.5 wt. %, based on the total weight of the oil phase.

The amount of hydrophobic polymer in the multiphase cleansing compositions will vary and will depend on the amount of hydrophobic polymer in the oil phase and the amount of oil phase combined with the aqueous phase to form the multiphase cleansing composition. Nonetheless, in various embodiments, the total amount of the hydrophobic polymer is from about 0.01 to about 2 wt. %, based on the total weight of the multiphase cleansing composition. In further embodiments, the total amount of the hydrophobic polymer is from about 0.01 to about 1.8 wt. %, about 0.01 to about 1.5 wt. %, about 0.01 to about 1.2 wt. %, about 0.01 to about 1 wt. %, about 0.02 to about 2 wt. %, about 0.02 to about 1.8 wt. %, about 0.02 to about 1.5 wt. %, about 0.02 to about 1.2 wt. %, about 0.02 to about 1 wt. %, about 0.05 to about 2 wt. %, about 0.05 to about 1.8 wt. %, about 0.05 to about 1.5 wt. %, about 0.05 to about 1.2 wt. %, about 0.05 to about 1 wt. %, based on the total weight of the multiphase cleansing composition.

(b) Solvent Capable of Solubilizing (a)

The oil phase of the multiphase cleansing composition includes the hydrophobic polymer of (a) dissolved in one or more solvents capable of solubilizing the hydrophobic polymer of (a). The solvent may include one or more solvents used to generate the hydrophobic polymer of (a), i.e., used in generating the reaction product, which is the hydrophobic polymer, such as, 2,2,4-trimethyl-1,3-pentanediol-monoisobutyrate. The solvent may be a single solvent or a plurality of solvents. For example, in various embodiments, solvents capable of solubilizing the hydrophobic polymer of (a) has a dispersion component (D), a polar component (P), a hydrogen bonding component (H), and a distance (Ra) of less than or equal to 13.4 $MPa^{0.5}$ per the Hansen Solubility Parameters, wherein the distance (Ra) is defined by formula (I):

$$Ra = \sqrt{4(D - D_1)^2 + (P - P_1)^2 + (H - H_1)^2} \quad \text{(I)}$$

wherein
$D_1$ is 16.8 $MPa^{0.5}$,
$P_1$ is 4.8 $MPa^{0.5}$, and
$H_1$ is 13.0 $MPa^{0.5}$.

In a preferred embodiment, the one or more solvents have a dispersion component (D), a polar component (P), a hydrogen bonding component (H), and a distance (Ra) of less than or equal to 9.9 $MPa^{0.5}$ per Hansen Solubility Parameters, wherein the distance (Ra) is defined by formula (I):

$$Ra = \sqrt{4(D - D_1)^2 + (P - P_1)^2 + (H - H_1)^2} \quad \text{(I)}$$

wherein
$D_1$ is 16.4 $MPa^{0.5}$,
$P_1$ is 5.0 $MPa^{0.5}$, and
$H_1$ is 11.7 $MPa^{0.5}$.

The solvent may be an oil. The term "oil" is intended to mean a non-aqueous compound, non-miscible in water, and liquid at 25° C. and atmospheric pressure (760 mmHg; $1.013\times10^5$ Pa). The solvent may be a non-silicone oil (e.g., an oil that does not contain silicon atoms, and in particular does not contain Si—O groups). Nonlimiting examples of solvents include caprylic/capric triglyceride, isopropyl myristate, and polycitronellol acetate. The solvent may include acetone. The solvent may include oleic acid. The solvent may include an oleic acid containing oil (such as a vegetable oil). Table 1 below, shows values of D, P, and H, as well as Ra for the allowable ranges as well as preferred ranges, for several preferred solvents.

TABLE 1

| Solvent (b) | D | P | H | Ra (Allowable Range) | Ra (Preferred Range) |
|---|---|---|---|---|---|
| Ethanol | 15.8 | 8.8 | 19.4 | 7.81 | 8.67 |
| Octyldodecanol | 16.1 | 2.2 | 7.4 | 6.33 | 5.17 |
| Isopropyl Myristate | 15.9 | 2.1 | 2.8 | 10.70 | 9.41 |
| Isopropyl Alcohol | 15.8 | 6.1 | 6.4 | 7.02 | 5.54 |
| Phenoxyethanol | 17.8 | 5.7 | 14.3 | 2.55 | 3.88 |
| CCTG | 18.22 | 5.39 | 14.74 | 3.38 | 4.76 |
| Castor Oil | 15.9 | 4.6 | 12 | 2.07 | 1.12 |
| Polycitronellol Acetate | 16.4 | 3 | 4.2 | 9.02 | 7.76 |
| Acetone | 15.5 | 10.4 | 7 | 8.61 | 7.38 |
| Oleic Acid | 16 | 2.8 | 6.2 | 7.27 | 5.98 |

In some embodiments, if oleic acid is utilized, at least some of the oleic acid may be provided by a vegetable oil. The vegetable oil may be a seed or nut oil. The vegetable oil may have an oleic acid content of at least 20% by weight of the vegetable oil. The vegetable oil may include sunflower oil, soybean oil, macadamia nut oil, and/or avocado oil. In some embodiments, the composition may include macadamia nut oil, and may be free, or substantially free, of other vegetable oils.

For purposes of the instant disclosure, the one or more of the solvents capable of solubilizing the hydrophobic polymer of (a) may not individually solubilize the hydrophobic polymer but when combined with other solvents, the combination solubilizes the hydrophobic polymer. Thus, when referring to a total amount of one or more solvents capable of solubilizing the hydrophobic polymer, the inclusion of all solvents that in combination solubilize the hydrophobic polymer is intended, even if one or more solvents in the combination do not individually solubilize the hydrophobic polymer.

Nonlimiting examples of solvents useful for solubilizing the hydrophobic polymer of (a), individually, or in combination with other solvents, include polycitronellol acetate, caprylic/capric triglyceride, isododecane, isohexadecane, tetradecane, isopropyl myristate, octyldodecanol, ethanol, phenoxyethanol, castor oil, and mixtures thereof. In a preferred embodiment, at least one of the one or more solvents capable of solubilizing the hydrophobic polymer are selected from caprylic/capric triglyceride, polycitronellol acetate, isododecane, and mixtures thereof. In another preferred embodiment, at least one of the one or more solvents capable of solubilizing the hydrophobic polymer is polycitronellol acetate.

Nonlimiting solvent that individually or in combination with other solvents are useful for solubilizing the hydrophobic polymer of (a) include dioctylcyclohexane, mineral oil, isocetyl palmitate, isocetyl palmitate, cyclopentasiloxane, dicaprylyl carbonate, octyl isostearate, trimethylhexyl isononanoate, 2-ethylhexyl isononanoate, dicaprylyl ether, dihexyl carbonate, polydecene, octyl cocoate, isodecyl neopentanoate, isohexy decanoate, isodecyl octanoate, dihexyl ether, isododecane, isodecyl 3,5,5 trimethyl hexanoate, oleyl erucate, *Passiflora incarnata* oil, jojoba oil, octyl palmitate, macadamia nut oil, isopropyl stearate, rapeseed oil, hexyl decanol, isotridecyl 3,5,5 trimethylhexanonanoate, polycitronellol acetate, mixed decanoyl and octanoyl glycerides, 2-ethylhexanoic acid, 3,5,5 trimethyl ester, cetystearyl octanoate, dimethicone, isopropyl palmitate, octyldodecanol, dioctyl adipate, isopropyl myristate, octyl palmitate (2-ethylhexyl palmitate), octyldodeceyl myristate, butyl octanoic acid, isopropyl stearate, caprylic/capric triglycerides, isopropyl isostearate, Jojoba oil, cyclomethicone, groundnut oil, almond oil, sunflower oil, decyl oleate, avocado oil, olive oil, dibutyl adipate, castor oil, calendula oil, wheatgerm oil, decyl oleate, avocado oil, calendula oil, propylene glycol monoisostearate, cocoglycerides, butylene glycol caprylate/caprate, C12-15 alkyl benzoate, caprylic/capric diglyceryl succinate, caprylic/capric triglyceride, cetearyl isonoanoate, cetearyl octanoate, cetyl dimethicone, coco-caprylate/caprate, cocoglycerides, Di-C12-13 alkyl tartrate, dibutyl adipate, dicaprylyl carbonate, dicaprylyl ether, hexyl decanol, hydrogenated polyisobutene, isoeicosane, isohexadecane, isopropyl palmitate, isopropyl stearate, octyl cocoate, octyl isostearate, octyl octanoate, octyl palmitate, octyl stearate, octyl dodecanol, octyldodecyl myristate, isopropyl stearate, pentaerythrityl tetraisostearate, phenyl trimethicone, polydecene, propylene glycol dicaprylate/dicaprate, stearyl heptanoate, tricaprylin, tridecyl stearate, tridecyl trimellitate, triisostearin, or combinations thereof.

The one or more solvents capable of solubilizing the hydrophobic polymer of (a) are often the predominant component of the oil phase. Therefore, the one or more solvents may constitute from about 60 to about 99.9 wt. % of the oil phase. The oil phase is not 100 wt. % of solvents because it includes the hydrophobic polymer of (a). In various embodiments, the oil phase includes from about 60 to about 99.9 wt. %, about 70 to about 99.9 wt. %, about 80 to about 99.9 wt. %, about 90 to about 99.9 wt. %, or about 95 to about 99.9 wt. % of the one or more solvents capable of solubilizing the hydrophobic polymer. In further embodiments, the oil phase may include from about 60 to about 99 wt. %, about 70 to about 99 wt. %, about 80 to about 99 wt. %, about 90 to about 99 wt. %, or about 95 to about 99 wt. % of the one or more oils capable of solubilizing the hydrophobic polymer, based on the total weight of the oil phase.

The total amount of the one or more oils capable of solubilizing the hydrophobic polymer of (a) in the multiphase cleansing composition will vary, depending on the amount of aqueous phase. Nonetheless, the total amount of the one or more oils capable of solubilizing the hydrophobic polymer of (a) may be from about 15 wt. % to about 65 wt. %, based on the total weight of the multiphase cleansing composition. The multiphase cleansing composition may include from about 15 to about 60 wt. %, about 15 to about 55 wt. %, about 15 to about 50 wt. %, about 15 to about 45 wt. %, about 15 to about 40 wt. %, about 20 to about 65 wt. %, about 20 to about 60 wt. %, about 20 to about 55 wt. %, about 20 to about 50 wt. %, about 20 to about 45 wt. %, about 20 to about 40 wt. %, about 25 to about 65 wt. %, about 25 to about 60 wt. %, about 25 to about 55 wt. %, about 25 to about 50 wt. %, about 25 to about 45 wt. %, about 25 to about 40 wt. %, about 30 to about 65 wt. %, about 30 to about 60 wt. %, about 30 to about 55 wt. %, about 30 to about 50 wt. %, about 30 to about 45 wt. %, or about 30 to about 40 wt. % of the one or more oils capable of solubilizing the hydrophobic polymer of (a), based on the total weight of the multiphase cleansing composition.

Oil Phase

The amount of oil phase in the multiphase cleansing composition will vary. The oil phase includes the hydrophobic polymer of (a), the one or more solvents capable of solubilizing the hydrophobic polymer of (a) and additional components that are miscible in the oil phase. For example, the oil phase may include one or more lipophilic active ingredients, one or more lipophilic film forming polymers, one or more lipophilic pigments, one or more lipophilic thickeners, one or more lipophilic vitamins or mineral, etc.

The amount of oil phase may be from about 15 wt. % to about 65 wt. %, based on the total weight of the multiphase cleansing composition. The multiphase cleansing composition may include from about 15 to about 60 wt. %, about 15 to about 55 wt. %, about 15 to about 50 wt. %, about 15 to about 45 wt. %, about 15 to about 40 wt. %, about 20 to about 65 wt. %, about 20 to about 60 wt. %, about 20 to about 55 wt. %, about 20 to about 50 wt. %, about 20 to about 45 wt. %, about 20 to about 40 wt. %, about 25 to about 65 wt. %, about 25 to about 60 wt. %, about 25 to about 55 wt. %, about 25 to about 50 wt. %, about 25 to about 45 wt. %, about 25 to about 40 wt. %, about 30 to about 65 wt. %, about 30 to about 60 wt. %, about 30 to about 55 wt. %, about 30 to about 50 wt. %, about 30 to about 45 wt. %, or about 30 to about 40 wt. %, based on the total weight of the multiphase cleansing composition.

(c) Water

The total amount of water in the multiphase cleansing composition will vary. Nonetheless, in various embodiments, the multiphase cleansing composition includes about 20 to about 80 wt. % of water, based on the total weight of the multiphase cleansing composition. In further embodiments, the multiphase cleansing composition include about 20 to about 75 wt. %, about 20 to about 70 wt. %, about 20 to about 65 wt. %, about 20 to about 60 wt. %, about 25 to about 75 wt. %, about 25 to about 70 wt. %, about 25 to about 65 wt. %, about 25 to about 60 wt. %, about 30 to about 75 wt. %, about 30 to about 70 wt. %, about 30 to about 65 wt. %, about 30 to about 60 wt. %, about 35 to about 75 wt. %, about 35 to about 70 wt. %, about 35 to about 65 wt. %, about 35 to about 60 wt. %, about 40 to about 75 wt. %, about 40 to about 70 wt. %, about 40 to about 65 wt. %, or about 40 to about 60 wt. % of water, based on the total weight of the multiphase cleansing composition.

(d) Water Soluble Solvent

The term "water soluble solvent" is interchangeable with the terms "water soluble organic solvent" and "water-miscible solvent" and means a compound that is liquid at 25° C. and at atmospheric pressure (760 mmHg), and it has a solubility of at least 50% in water under these conditions. In some cases, the water-soluble solvents have a solubility of at least 60%, 70%, 80%, or 90%. Non-limiting examples of water-soluble solvents include, for example, organic solvents selected from glycerin, alcohols (for example $C_{1-8}$, or $C_{1-4}$ alcohols), polyols (polyhydric alcohols), glycols, and a mixture thereof.

Nonlimiting examples of water-soluble organic solvents. Non-limiting examples of water-soluble organic solvents include, for example, organic solvents selected from alcohols (for example $C_{2-6}$ or $C_{2-4}$ alcohols), polyols (polyhydric alcohols), glycols, and a mixture thereof. Nonlimiting examples of monoalcohols and polyols include ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, and propane diol.

Further non-limiting examples of water soluble organic solvents include alkanediols (polyhydric alcohols) such as 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In a preferred embodiment, the multiphase cleansing composition includes one or more glycols selected from propylene glycol, butylene glycol, pentylene glycol, hexylene glycol, caprylyl glycol, dipropylene glycol, and mixtures thereof.

The total amount of the one or more water soluble solvents in the multiphase cleansing composition will vary. Nonetheless, in various embodiment, the multiphase cleansing composition include about 0.1 to about 30 wt. % of one or more water soluble solvents, based on the total weight of the compositions. In further embodiments, the compositions include about 0.1 to about 25 wt. %, about 0.1 to about 20 wt. %, about 0.1 to about 15 wt. %, about 0.5 to about 30 wt. %, about 0.5 to about 25 wt. %, about 0.5 to about 20 wt. %, about 0.5 to about 15 wt. %, about 1 to about 30 wt. %, about 1 to about 25 wt. %, about 1 to about 20 wt. %, about 1 to about 15 wt. %, about 2 to about 30 wt. %, about 2 to about 25 wt. %, about 2 to about 20 wt. %, about 2 to about 15 wt. %, about 5 to about 30 wt. %, about 5 to about 25 wt. %, about 5 to about 20 wt. %, about 5 to about 15 wt. %, about 10 to about 30 wt. %, about 10 to about 25 wt. %, about 10 to about 20 wt. % of one or more water soluble solvents, based on the total weight of the composition.

(e) Electrolyte

The multiphase cleansing composition may include one or more electrolytes. The addition of electrolyte may assist in adjusting composition viscosity. Electrolytes are materials that dissolve in water and ionize. The term excludes materials such as surfactants, as well as other materials that aggregate in solution. Among the electrolytes suitable for use herein are simple salts of organic or inorganic acids. Chlorides, nitrates, sulfates, and carboxylates are among the suitable salts. Examples of suitable electrolytes are sodium chloride, ammonium chloride, magnesium chloride, sodium sulfate and sodium citrate. Typically, the electrolytes are relatively small molecules that frequently have nominal molecular weights of less than 600 g/mol.

When present, the total amount of the one or more electrolytes is from about 0.1 to about 20 wt. %, based on the total weight of the aqueous phase. In further embodiments, the total amount of the one or more electrolytes is from about 0.1 to about 15 wt. %, about 0.1 to about 10 wt. %, about 0.1 to about 5 wt. %, about 0.5 to about 20 wt. %, about 0.5 to about 15 wt. %, about 0.5 to about 10 wt. %, about 0.5 to about 5 wt. %, about 1 to about 20 wt. %, about 1 to about 15 wt. %, about 1 to about 10 wt. %, about 1 to about 5 wt. %, based on the total weight of the aqueous phase.

In regards to the multiphase cleansing composition, the total amount of the one or more electrolytes may be from about 0.1 to about 15 wt. %, based on the total weight of the multiphase cleansing composition. In further embodiments, the total amount of the one or more electrolytes in the multiphase cleansing composition is from about 0.1 to about 12 wt. %, about 0.1 to about 10 wt. %, about 0.1 to about 8 wt. %, about 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, about 0.5 to about 3 wt. %, about 1 to about 15 wt. %, about 1 to about 12 wt. %, about 1 to about 10 wt. %, about 1 to about 8 wt. %, about 1 to about 5 wt. %, about 1 to about 3 wt. %, about 2 to about 15 wt. %, about 2 to about 12 wt. %, about 2 to about 10 wt. %, about 2 to about 8 wt. %, about 2 to about 5 wt. %, or about 2 to about 4 wt. %, based on the total weight of the multiphase cleansing composition.

Aqueous Phase

The aqueous phase may be referred to as the "water phase" and includes water and components soluble in the aqueous phase. For example, the aqueous phase may include water, one or more water soluble solvents, one or more electrolytes, one or more hydrophilic film forming polymers, one or more aqueous thickening agents, one or more water soluble active agents, and the like. The amount of aqueous phase in the multiphase cleansing composition will vary. Nonetheless, the amount of aqueous may be from about 25 wt. % to about 80 wt. %, based on the total weight of the multiphase cleansing composition. The multiphase cleansing composition may include from about 25 to about 75 wt. %, about 25 to about 70 wt. %, about 25 to about 65 wt. %, about 30 to about 80 wt. %, about 30 to about 75 wt. %, about 30 to about 70 wt. %, about 35 to about 80 wt. %, about 35 to about 75 wt. %, about 35 to about 70 wt. %, about 40 to about 80 wt. %, about 40 to about 75 wt. %, about 40 to about 70 wt. %, about 45 to about 80 wt. %, about 45 to about 75 wt. %, about 45 to about 70 wt. %, about 50 to about 80 wt. %, about 50 to about 75 wt. %, about 50 to about 70 wt. %, about 55 to about 80 wt. %, about 55 to about 75 wt. %, or about 55 to about 70 wt. %, based on the total weight of the multiphase cleansing composition.

Thickening Agents

The multiphase cleansing compositions may optionally include one or more thickening agents. The thickening agents may be lipophilic or hydrophilic, i.e., they may be appropriate for thickening the oil phase or appropriate for thickening the aqueous phase.

Non-limiting examples of thickening agents useful for thickening an oil phase include C12-22 alkyl acrylate/hydroxyethylacrylate copolymer (INTELIMER), ethylene diamine/stearyl dimer dilinoleate copolymer such as OLEOCRAFT LP-10-PA-(MV) sold by Croda, polyamide-8 such as OLEOCRAFT LP-20-PA-(MV) sold by Croda, poly $C_{10}$-$C_{30}$ alkyl acrylate such as INTELIMER IPA 13-6 or INTELIMER IPA 13-1 NG Polymer sold by Air Products & Chemicals, and nylon-611/dimethicone copolymer such as Dow Corning 2-8179 Gellant sold by Dow Corning, dextrin palmitate such as RHEOPEARL KL2-OR sold by Chiba Flour Milling. Additional non-limiting examples of non-mineral thickening agents useful for thickening anhydrous compositions include thickening polymers such block copolymers of styrene with ethylene propylene and/or butylene available under the trade name KRATON, and particularly styrene ethylene/butylene styrene linear block copolymers. A related category of thickening polymer comprises polymers of alpha methylstyrene and styrene, such as those under the trade name KRISTALEX. Yet another thickening polymer comprises alkyl substituted galactomannan available under the trade name N-HANCE AG. Thickening agents useful for thickening oil phases may also include thickening polymers such as vinyl pyrrolidone with polyethylene containing at least 25 methylene units, such as triacontanyl polyvinylpyrrolidone, under the trade name Antaron WP-660.

Non-limiting examples of thickening agents useful for thickening aqueous phases include xanthan gum, guar gum, biosaccharide gum, cellulose, acacia Seneca gum, *sclerotium* gum, agarose, pechtin, gellan gum, hyaluronic acid. Additionally, the one or more thickening agents may be polymeric thickeners such as, for example, ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer, and sodium acrylates crosspolymer-2, which is commercially available as AQUA-KEEP 10SH-NFC as sodium acrylates crosspolymer-2 (and) water (and) silica.

Additional, non-limiting examples of various types of thickening agents include:

i. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez®10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

ii. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 4,599,379 and EP 228,868, which are all incorporated herein by reference in their entirety.

iii. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

iv. Polysaccharides

A wide variety of polysaccharides can be useful herein. "Polysacchaides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

v. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

The total amount of the one or more thickening agents, if present, will vary. Nonetheless, if present, the total amount of the one or more thickening agents may be from about 0.01 to about 15 wt. %, based on the total weight of the multiphase cleansing composition. In some instances, the total amount of the one or more thickening agents may be about 0.01 to about 10 wt. %, about 0.01 to about 5 wt. %, about 0.1 to about 15 wt. %, about 0.1 to about 10 wt. %, or about 0.1 to about 5 wt. %, based on the total weight of the multiphase cleansing composition.

Surfactants

The multiphase cleansing compositions may optionally include one or more surfactants. However, as mentioned above, surfactants are not required, and the multiphase cleansing compositions may be free or essentially free from surfactants. On the hand, in certain instances, it may be beneficial to incorporate one or more surfactants. The one or more surfactants may be selected from anionic surfactants, nonionic surfactants, amphoteric (zwitterionic) surfactants, and cationic surfactants. Moreover, the multiphase cleansing compositions may include one or more biosurfactants.

For purposes of the instant disclosure, the term "surfactant" includes emulsifiers and detergents and encompasses co-surfactants. Surfactants, or surface-active agents, are compounds that lower the surface tension between two liquids or between a liquid and a solid. Surfactants are amphiphilic, meaning that they contain hydrophilic (water-loving) head groups and hydrophobic (water-hating, or oil-loving) tails. Surfactants adsorb at the interface between oil and water, thereby decreasing the surface tension.

For purposes of the instant disclosure, an "emulsifier" is a surfactant that stabilizes compositions. Emulsifiers coat droplets within a dispersion and prevent them from coming together, or coalescing. An "emulsion" is a mixture of two or more liquids, with or without an emulsifier, that are normally immiscible. One of the liquids, the "dispersed phase," forms droplets in the other liquid, the "continuous phase." A "detergent" is a surfactant that has cleaning properties in dilute solutions and is typically anionic. A "dispersion" according to the instant disclosure is an emulsion having the oil phase (lipophilic phase) in droplets having an average diameter of from about 10 nm to about 2 μm.

The multiphase cleansing compositions of the instant disclosure typically have a homogenous aqueous phase and a homogenous oil phase. The aqueous phase may solubilizes/dissolve the components of the aqueous phase, and the oil phase may solubilize/dissolve the components of the oil phase. In other embodiments, however, the aqueous phase or the oil phase may be in the form of emulsions such that the aqueous phase includes fatty droplets or insoluble particles dispersed throughout the aqueous phase and/or the oil phase may have aqueous droplets or insoluble particles dispersed throughout the oil phase. Depside the oil droplets dispersed throughout the aqueous phase, the aqueous phase is not miscible with the oil phase, i.e., the multiphase composition still phase separate into an aqueous phase and an oil phase, but the aqueous phase contains oil droplets or insoluble particles dispersed therein.

Surfactants are characterized as anionic, cationic, amphoteric (zwitterionic), or nonionic. In various embodiments, the multiphase cleansing composition includes one or more surfactants, for example, one or more surfactants selected from anionic surfactants, nonionic surfactants, amphoteric (zwitterionic) surfactants, cationic surfactants, or mixtures thereof. For example, the aqueous phase may include one or more anionic surfactants, one or more amphoteric surfactants, one or more nonionic surfactants, or combinations thereof. Inclusion of one or more anionic surfactants can be useful in the aqueous phase for their cleansing and foaming properties. Therefore, in certain embodiments, the aqueous phase includes one or more anionic surfactants.

Anionic Surfactants

Popular anionic surfactants known for their good detersive and foaming properties include sodium lauryl sulfate and sodium laureth ether sulfate. Sulfate-based surfactants may optionally be included. In other embodiments, it is preferable that the multiphase cleansing composition is free or essentially free from sulfate-based surfactants. In some instances, it can be useful to include a gentler, non-sulfate anionic surfactant, such as one or more anionic surfactants selected from alkyl sulfonates, alkyl sulfosuccinates, alkyl sulfoacetates, acyl isethionates, alkoxylated monoacids, acyl amino acids such as acyl taurates, acyl glycinates, acyl glutamates, acyl sarcosinates, salts thereof, or mixtures thereof.

(a) Acyl Isethionates

Non-limiting examples of useful acyl isethionates include those of formula (III) and (IV):

(III)

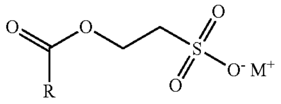

(IV)

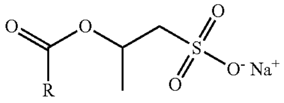

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. Although sodium is shown as the cation in formulae (III) and (IV), the cation for both formula (III) and formula (IV) may be an alkali metal ion such as sodium or potassium, ammonium ions, or alkanolammonium ions such as monoethanolammonium or triethanolammonium ions. Non-limiting examples of acyl isethionates include sodium isethionate, sodium cocoyl isethionate, sodium lauroyl methyl isethionate, and sodium cocoyl methyl isethionate. In some embodiments, a combination of sodium isethionate and sodium cocoyl isethionate are preferable.

(b) Alkyl Sulfonates

Examples of alkyl sulfonates include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenvlalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some instances, an alkyl sulfonate of formula (V) is particularly useful.

(V)

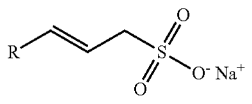

R is selected from H or alkyl chain that has 1-24 carbon atoms, preferably 6-24 carbon atoms, more preferably, 8 to 20 carbon atoms, said chain being saturated or unsaturated, linear or branched. Sodium is shown as the cation in the above formula (V) but the cation may be an alkali metal ion such as sodium or potassium, ammonium ions, or alkanolammonium ions such as monoethanolammonium or triethanolammonium ions. In some instances, the alkyl sulfonate(s) are selected from $C_8$-$C_{16}$ alkyl benzene sulfonates, $C_{10}$-$C_{20}$ paraffin sulfonates, $C_{10}$-$C_{24}$ olefin sulfonates, salts thereof, and mixtures thereof. $C_{10}$-$C_{24}$ olefin sulfonates may be particularly preferred. A non-limiting example of a $C_{10}$-$C_{24}$ olefin sulfonate that can be used in the instant compositions is sodium $C_{14}$-$C_{16}$ olefin sulfonate.

(c) Alkyl Sulfosuccinates

Non-limiting examples of useful sulfosuccinates include those of formula (VI):

(VI)

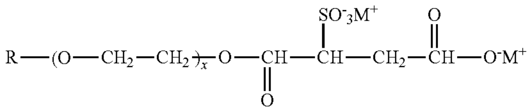

wherein R is a straight or branched chain alkyl or alkenyl group having 10 to 22 carbon atoms, preferably 10 to 20 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. Preferred cations are alkali metal ions such as sodium or potassium, ammonium ions, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a mixture thereof. In some instances, disodium laureth sulfosuccinate is particularly preferred.

(d) Alkyl Sulfoacetates

Non-limiting examples of alkyl sulfacetates includes, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

(e) Alkoxylated Monoacids

Non-limiting examples of alkoxylated monoacids include compounds corresponding to formula (VII):

(VII)

RO[CH2O]u[(CH2)xCH(R')(CH2)y(CH2)zO]v[CH2CH2O]wCH2COOH wherein:

- R is a hydrocarbon radical containing from about 6 to about 40 carbon atoms;
- u, v and w, independently of one another, represent numbers of from 0 to 60;
- x, y and z, independently of one another, represent numbers of from 0 to 13;
- R' represents hydrogen, alkyl, and
- the sum of x+y+z>0;
- Compounds corresponding to formula (VII) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (VII), R is linear or branched, acyclic or cyclic, saturated or unsaturated, aliphatic or aromatic, substituted or unsubstituted. Typically, R is a linear or branched, acyclic $C_6$-$C_{40}$ alkyl or alkenyl group or a $C_1$-$C_{40}$ alkyl phenyl group, more typically a $C_8$-$C_{22}$ alkyl or alkenyl group or a $C_4$-$C_{18}$ alkyl phenyl group, and even more typically a $C_{12}$-$C_{18}$ alkyl group or alkenyl group or a $C_6$-$C_{16}$ alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, $C_9$-$C_{11}$ Pareth-6 Carboxylic Acid, $C_{11}$-$C_{15}$ Pareth-7 Carboxylic Acid, $C_{12}$-$C_{13}$ Pareth-5 Carboxylic Acid, $C_{12}$-$C_{13}$ Pareth-8 Carboxylic Acid, $C_{12}$-$C_{13}$ Pareth-12 Carboxylic Acid, $C_{12}$-$C_{15}$ Pareth-7 Carboxylic Acid, $C_{12}$-$C_{15}$ Pareth-8 Carboxylic Acid, $C_{14}$-$C_{15}$ Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof. In some cases, preferred ethoxylated acids include Oleth-10 Carboxylic Acid, Laureth-5 Carboxylic Acid, Laureth-11 Carboxylic Acid, and a mixture thereof.

(t) Acyl Amino Acids

Acyl amino acids that may be used include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. The most common cation associated with the acyl amino acid can be sodium or potassium. Alternatively, the cation can be an organic salt such as triethanolamine (TEA) or a metal salt. Non-limiting examples of acyl amino acids include those of formula (VIII):

(VIII)

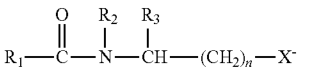

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$.

(g) Acyl Taurates

Non-limiting examples of acyl taurates include those of formula (IX):

(IX)

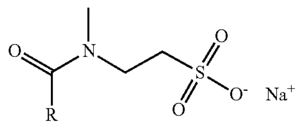

wherein R, $R^1$, $R^2$ and $R^3$ are each independently selected from H or an alkyl chain having 1-24 carbon atoms, or from 6-20 carbon atoms, or from 8 to 16 carbon atoms, said chain being saturated or unsaturated, linear or branched, and X is $COO^-$ or $SO_3^-$. Non-limiting examples of acyl taurate salts include sodium cocoyl taurate, sodium methyl cocoyl taurate, sodium lauroyl taurate, and sodium methyl lauroyl taurate.

(h) Acyl Glycinates

Non-limiting examples of acyl glycinates include those of formula (X):

(X)

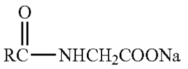

wherein R is an alkyl chain of 8 to 16 carbon atoms. Although sodium is shown as the cation in the above formula (X), the cation may be an alkali metal ion such as sodium or potassium, ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and in particular sodium cocoyl glycinate.

(i) Acyl Glutamates

Non-limiting examples of acyl glutamates include those of formula (XI):

(XI)

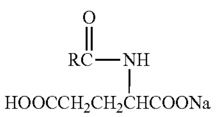

wherein R is an alkyl chain of 8 to 16 carbon atoms. Sodium is shown as the cation in the above formula (XI) but the cation may be an alkali metal ion such as sodium or potassium, ammonium ions, or alkanolammonium ions such as monoethanolammonium or triethanolammonium ions. Non-limiting examples of acyl gluatamtes include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly preferred.

(j) Acyl Sarcosinates:

Non-limiting examples of acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate.

The total amount of one or more anionic surfactants, if present, may be from about 0.01 to about 10 wt. %, based on the total weight of the aqueous phase. In further embodiments, the aqueous phase includes from about 0.01 to about 8 wt. %, about 0.01 to about 6 wt. %, about 0.01 to about 5 wt. %, about 0.01 to about 3 wt. %, about 0.1 to about 10 wt. %, about 0.1 to about 8 wt. %, about 0.1 to about 6 wt. %, about 0.1 to about 5 wt. %, about 0.1 to about 3 wt. %, about 0.5 to about 10 wt. %, about 0.5 to about 8 wt. %, about 0.5 to about 6 wt. %, about 0.5 to about 5 wt. %, about 0.5 to about 3 wt. %, about 1 to about 10 wt. %, about 1 to about 8 wt. %, about 1 to about 6 wt. %, about 1 to about 5 wt. %, or about 1 to about 3 wt. % of the one or more anionic surfactants, based on the total weight of the aqueous phase.

The total amount of the one or more anionic surfactants relative to the total weight of the multiphase cleansing composition, if present, may be from about 0.01 to about 6 wt. %, based on the total weight of the multiphase cleansing composition. In further embodiments, the total amount of the one or more anionic surfactants relative to the total weight of the multiphase cleansing composition, if present, is from about 0.01 to about 5 wt. %, about 0.01 to about 3 wt. %, about 0.1 to about 6 wt. %, about 0.1 to about 5 wt.

%, about 0.1 to about 3 wt. %, about 0.5 to about 6 wt. %, about 0.5 to about 5 wt. %, about 0.5 to about 3 wt. %, based on the total weight of the multiphase cleansing composition.

Amphoteric Surfactants

The multiphase cleansing compositions may optionally include one or more amphoteric surfactants. Nonlimiting examples of amphoteric surfactants include betaines, alkyl amphoacetates and alkyl amphodiacetates, alkyl sulltaines, alkyl amphopropionates, and combinations thereof.

Nonlimiting examples of betaine surfactants include coco-betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, or mixtures thereof.

Nonlimiting examples of alkyl amphoacetates and alkyl amphodiacetates include (C8-C20)alkylamphoacetates and (C8-C20)alkylamphodiacetates, such as disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caprylomphodipropionate, lauroamphodipropionic acid, cocoamphodipropionic acid, and combinations thereof.

The total amount of the one or more amphoteric surfactants, if present, may be from about 0.01 to about 10 wt. %, based on the total weight of the aqueous phase. In further embodiments, the total amount of the one or more amphoteric surfactants is from about 0.01 to about 8 wt. %, about 0.01 to about 6 wt. %, about 0.01 to about 5 wt. %, about 0.01 to about 3 wt. %, based on the total weight of the aqueous phase.

The total amount of the one or more amphoteric surfactants relative to the total weight of the multiphase cleansing composition, if present, may be from about 0.01 to about 5 wt. %, based on the total weight of the multiphase cleansing composition. In further embodiments, the total amount of the one or more amphoteric surfactants relative to the total weight of the multiphase cleansing composition, if present, is from about 0.01 to about 4 wt. %, about 0.01 to about 3 wt. %, about 0.1 to about 5 wt. %, about 0.1 to about 4 wt. %, or about 0.1 to about 3 wt. %, based on the total weight of the multiphase cleansing composition.

Nonionic Surfactants

The multiphase cleansing composition may optionally include one or more nonionic surfactants. Nonlimiting examples of nonionic surfactants include alkoxylated fatty alcohols, alkoxylated polyol esters, alkoxylated glycerides, glucosides, alkanolamides, sorbitan derivatives, or combinations thereof.

Nonlimiting examples of alkoxylated fatty alcohols include laureth-3, laureth-4, laureth-7, laureth-9, laureth-12, laureth-23, ceteth-10, steareth-10, steareth-2, steareth-100, beheneth-5, beheneth-5, beheneth-10, oleth-10, Pareth alcohols, trideceth-10, trideceth-12, C12-13 pareth-3, C12-13 pareth-23, C11-15 pareth-7, PEG hydrogenated castore oil, PEG-75 lanolin, polysorbate-80, polysobate-20, PPG-5 ceteth-20, PEG-55 Propylene Glycol Oleate, glycereth-26 (PEG-26 Glyceryl Ether), PEG 120 methyl glucose dioleate, PEG 120 methyl glucose trioleate, PEG 150 pentaerythrityl tetrastearate, and mixtures thereof.

Nonlimiting examples of alkoxylatecd polyol esters include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the INCI names: PEG-9 laurate to PEG-50 laurate); PEG-9 to PEG-50 palmitate (as the INCI names: PEG-9 palmitate to PEG-50 palmitate); PEG-9 to PEG-50 stearate (as the INCI names: PEG-9 stearate to PEG-50 stearate); PEG-9 to PEG-50 palmitostearate; PEG-9 to PEG-50 behenate (as the INCI names: PEG-9 behenate to PEG-50 behenate); polyethylene glycol 100 EO monostearate (INCI name: PEG-100 stearate); and mixtures thereof.

Nonlimiting examples of alkoxylated glycerides include PEG-6 almond glycerides, PEG-20 almond glycerides, PEG-35 almond glycerides, PEG-60 almond glycerides, PEG-192 apricot kernel glycerides, PEG-11 avocado glycerides, PEG-14 avocado glycerides, PEG-11 babassu glycerides, PEG-42 babassu glycerides, PEG-4 caprylic/capric glycerides, PEG-6 caprylic/capric glycerides, PEG-7 caprylic/capric glycerides, PEG-8 caprylic/capric glycerides, PEG-11 cocoa butter glycerides, PEG-75 cocoa butter glycerides, PEG-7 cocoglycerides, PEG-9 cocoglycerides, PEG-20 corn glycerides, PEG-60 corn glycerides, PEG-20 evening primrose glycerides, PEG-60 evening primrose glycerides, PEG-5 hydrogenated corn glycerides, PEG-8 hydrogenated fish glycerides, PEG-20 hydrogenated palm glycerides, PEG-6 hydrogenated palm/palm kernel glyceride, PEG-16 macadamia glycerides, PEG-70 mango glycerides, PEG-13 mink glycerides, PEG-25 moringa glycerides, PEG-42 mushroom glycerides, PEG-2 olive glycerides, PEG-6 olive glycerides, PEG-7 olive glycerides, PEG-10 olive glycerides, PEG-40 olive glycerides, PEG-18 palm glycerides, PEG-12 palm kernel glycerides, PEG-45 palm kernel glycerides, PEG-60 *Passiflora edulis* seed glycerides, PEG-60 *Passiflora incarnata* seed glycerides, PEG-45 safflower glycerides, PEG-60 shea butter glycerides, PEG-75 shea butter glycerides, PEG-75 shorea butter glycerides, PEG-35 soy glycerides, PEG-75 soy glycerides, PEG-2 sunflower glycerides, PEG-7 sunflower glycerides, PEG-10 sunflower glycerides, PEG-13 sunflower glycerides, PEG-5 tsubakiate glycerides, PEG-10 tsubakiate glycerides, PEG-20 tsubakiate glycerides, PEG-60 tsubakiate glycerides, sodium PEG-8 palm glycerides carboxylate, or mixtures thereof.

Nonlimiting examples of glucosides (also known as "alkyl polyglucosides") include lauryl glucoside, octyl glucoside, decyl glucoside, coco glucoside, caprylyl/capryl glucoside, sodium lauryl glucose carboxylate, or combinations thereof.

Nonlimiting examples of alkanolamides include cocamide MIPA, cocamide DEA, cocamide MEA, cocamide DIPA, and mixtures thereof.

Nonlimiting examples of sorbitan derivatives include polysorbates, for example, polysorbate-20 (POE(20) sorbitan monolaurate), polysorbate-21 (POE(4) sorbitan monolaurate), polysorbate-40 (POE(20) sorbitan monopalmitate), polysorbate-60 (POE(20) sorbitan monostearate), polysorbate-61 (POE(4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), sorbitan isostearate, sorbitan monolaurate, sorbitan monooleate, sorbitan monopalmitate, sorbitan monostearate, sorbitan sesquioleate, sorbitan trioleate sorbitan tristearate, or mixtures thereof.

The total amount of the one or more nonionic surfactants, if present, may be from about 0.01 to about 10 wt. %, based on the total weight of the aqueous phase. In further embodiments, the total amount of the one or more nonionic surfactants is from about 0.01 to about 8 wt. %, about 0.01 to about 6 wt. %, about 0.01 to about 5 wt. %, about 0.01 to about 3 wt. %, based on the total weight of the aqueous phase.

The total amount of the one or more nonionic surfactants relative to the total weight of the multiphase cleansing composition, if present, may be from about 0.01 to about 5 wt. %, based on the total weight of the multiphase cleansing composition. In further embodiments, the total amount of the one or more nonionic surfactants relative to the total weight of the multiphase cleansing composition, if present, is from about 0.01 to about 4 wt. %, about 0.01 to about 3 wt. %, about 0.1 to about 5 wt. %, about 0.1 to about 4 wt. %, or about 0.1 to about 3 wt. %, based on the total weight of the multiphase cleansing composition.

Cationic Surfactants

Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyl dimethylamine, behenamidopropyl dimethylamine, behenamidopropyl diethylamine, behenamidoethyl diethylamine, behenamidoethyl dimethylamine, arachidamidopropyl dimethylamine, arachidamidopropyl diethylamine, arachidamidoethyl diethylamine, arachidamidoethyl dimethylamine, brassicamidopropyl dimethylamine, lauramidopropyl dimethylamine, myristamidopropyl dimethylamine, dilinoleamidopropyl dimethylamine, palmitamidopropyl dimethylamine, and mixtures thereof.

The one or more cationic surfactants may be selected from quaternary ammonium compounds, fatty dialkylamines, or mixtures thereof.

Nonlimiting examples of quaternary ammonium compounds include cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, and combinations thereof.

Nonlimiting examples of fatty dialkylamines include oleamidopropyl dimethylamine, linoleamidopropyl dimethylamine, isostearamidopropyl dimethylamine, oleyl hydroxyethyl imidazoline, stearamidopropyl dimethylamine, behenamidopropyl dimethylamine, behenamidopropyl diethylamine, behenamidoethyl diethylamine, behenamidoethyl dimethylamine, arachidamidopropyl dimethylamine, arachidamidopropyl diethylamine, arachidamidoethyl diethylamine, arachidamidoethyl dimethylamine, brassicamidopropyl dimethylamine, lauramidopropyl dimethylamine, myristamidopropyl dimethylamine, dilinoleamidopropyl dimethylamine, palmitamidopropyl dimethylamine, salts thereof, and combinations thereof.

In various embodiments, the one or more cationic surfactants are preferably selected from cetrimonium chloride, behentrimonium chloride, behentrimonium methosulfate, stearamidopropyl dimethylamine, brassicamidopropyl dimethylamine or a mixture thereof.

The total amount of the one or more cationic surfactants, if present, may be from about 0.01 to about 5 wt. %, based on the total weight of the multiphase cleansing composition. In further embodiments, the total amount of the one or more cationic surfactants is from about 0.01 to about 8 wt. %, about 0.01 to about 6 wt. %, about 0.01 to about 5 wt. %, about 0.01 to about 3 wt. %, based on the total weight of the multiphase cleansing composition.

Miscellaneous Ingredients

The compositions optionally include or exclude (or are essentially free from) one or more miscellaneous ingredients. Miscellaneous ingredients are ingredients that are compatible with the compositions and do not disrupt or materially affect the basic and novel properties of the compositions. Nonlimiting examples of ingredients include preservatives, fragrances, pH adjusters, chelating agents, buffers, antioxidants, flavonoids, vitamins, botanical extracts, UV filtering agents, proteins, protein hydrolysates, and/or isolates, fillers (e.g., organic and/or inorganic fillers such as talc, calcium carbonate, silica, etc.) composition colorants, etc. In various embodiments, the miscellaneous ingredients are chosen from preservatives, fragrances, pH adjusters, salts, chelating agents, buffers, composition colorants, and mixtures thereof. In the context of the instant disclosure, a "composition colorant" is a compound that colors the composition but does not have an appreciable coloring effect on hair. In other words, the composition colorant is included to provide a coloring to the composition for aesthetic appeal but is not intended to impart coloring properties to hair. Styling gels, for example, can be found in a variety of different colors (e.g., light blue, light pink, etc.) yet application of the styling gel to hair does not visibly change the color of the hair.

The total amount of the one or more miscellaneous ingredients in the multiphase cleansing compositions, if present, will vary. Nonetheless, in various embodiments, the multiphase cleansing compositions include about 0.1 to about 15 wt. % of the one or more miscellaneous ingredients, based on the total weight of the multiphase cleansing compositions. In further embodiments, the multiphase cleansing compositions include about 0.1 to about 12 wt. %, about 0.1 to about 10 wt. %, about 0.1 to about 5 wt. %, about 0.5 to about 15 wt. %, about 0.5 to about 12 wt. %, about 0.5 to about 10 wt. %, about 0.5 to about 8 wt. %, about 0.5 to about 5 wt. %, about 1 to about 15 wt. %, about 1 to about 12 wt. %, about 1 to about 10 wt. %, about 1 to about 8 wt. %, about 1 to about 5 wt. %, about 2 to about 15 wt. %, about 2 to about 12 wt. %, about 2 to about 10 wt. %, about 2 to about 8 wt. %, or about 2 to about 5 wt. % of one or more miscellaneous ingredients, based on the total weight of the multiphase cleansing compositions.

pH

The pH of the multiphase cosmetic composition will depend on the pH of the aqueous phase. The pH of the aqueous phase is typically from about 4.5 to about 8.5. Preferably, the pH of the aqueous phase is from about 5 to about 8, about 5 to about 7.5, about 5 to about 7, about 5.5 to about 8, about 5.5 to about 7.5, about 5.5 to about 7, about 6 to about 8, about 6 to about 7.5, or about 6 to about 7.

EMBODIMENTS

In preferred embodiments, the multiphase cleansing compositions comprise, consist of, or consist essentially of:

(a) about 0.01 to about 5 wt. %, preferably about 0.01 to about 3 wt. %, more preferably about 0.02 to about 3 wt. % of a hydrophobic polymer, which is a reaction product of a natural or food-derived oil and a methacrylate or acrylate polymer, wherein preferably,
    the hydrophobic polymer is a reaction product of: (a)(i) a natural or food-derived oil selected from linseed oil, sunflower oil, tung oil, fish oil, cottonseed oil, soybean oil, or combinations thereof, preferably linseed oil; and (a)(ii) a polymer derived from monomers selected from isobutyl methacrylate, methyl methacrylate, ethyl methacrylate, n-butyl methacrylate, and combinations thereof, preferably isobutyl methacrylate polymer, wherein even more preferably, the hydrophobic polymer is the reaction product of linseed oil and poly(isobutyl methacrylate);

(b) about 5 to about 60 wt. %, preferably about 25 to about 50 wt. %, more preferably 30 to about 45 wt. % of one or more solvents capable of solubilizing the reaction product of (a), wherein preferably, the one or more solvents capable of solubilizing the reaction product of (a) have a dispersion component (D), a polar component (P), and a hydrogen bonding component (H), and a distance (Ra) of less than or equal to 13.4 $MPa^{0.5}$ per Hansen Solubility Parameters, wherein the distance (Ra) is defined by formula (I):

$$Ra = \sqrt{4(D - D_1)^2 + (P - P_1)^2 + (H - H_1)^2} \quad (I)$$

wherein $D_1$ is 16.8 $MPa^{0.5}$, $P_1$ is 4.8 $MPa^{0.5}$, and $H_1$ is 13.0 $MPa^{0.5}$, wherein more preferably, the one or more solvents capable of solubilizing the reaction product of (a) have a dispersion component (D), a polar component (P), and a hydrogen bonding component (H), and a distance (Ra) of less than or equal to 9.9 $MPa^{0.5}$ per Hansen Solubility Parameters, wherein the distance (Ra) is defined by formula (I):

$$Ra = \sqrt{4(D - D_1)^2 + (P - P_1)^2 + (H - H_1)^2} \quad (I)$$

wherein $D_1$ is 16.4 $MPa^{0.5}$, $P_1$ is 5.0 $MPa^{0.5}$, and $H_1$ is 11.7 $MPa^{0.5}$, wherein even more preferably, at least one of the one or more solvents capable of dissolving the hydrophobic polymer of (a) are selected from dioctylcyclohexane, mineral oil, isocetyl palmitate, isocetyl palmitate, cyclopentasiloxane, dicaprylyl carbonate, octyl isostearate, trimethylhexyl isononanoate, 2-ethylhexyl isononanoate, dicaprylyl ether, dihexyl carbonate, polydecene, octyl cocoate, isodecyl neopentanoate, isohexy decanoate, isodecyl octanoate, dihexyl ether, isododecane, isodecyl 3,5,5 trimethyl hexanoate, oleyl erucate, *Passiflora incarnata* oil, jojoba oil, octyl palmitate, macadamia nut oil, isopropyl stearate, rapeseed oil, hexyl decanol, isotridecyl 3,5,5 trimethylhexanonanoate, polycitronellol acetate, mixed decanoyl and octanoyl glycerides, 2-ethylhexanoic acid, 3,5,5 trimethyl ester, cetystearyl octanoate, dimethicone, isopropyl palmitate, octyldodecanol, dioctyl adipate, isopropyl myristate, octyl palmitate (2-ethylhexyl palmitate), octyldodeceyl myristate, butyl octanoic acid, isopropyl stearate, caprylic/capric triglycerides, isopropyl isostearate, Jojoba oil, cyclomethicone, groundnut oil, almond oil, sunflower oil, decyl oleate, avocado oil, olive oil, dibutyl adipate, castor oil, calendula oil, wheatgerm oil, decyl oleate, avocado oil, calendula oil, propylene glycol monoisostearate, cocoglycerides, butylene glycol caprylate/caprate, $C_{12}$-15 alkyl benzoate, caprylic/capric diglyceryl succinate, caprylic/capric triglyceride, cetearyl isonoanoate, cetearyl octanoate, cetyl dimethicone, coco-caprylate/caprate, cocoglycerides, Di-C12-13 alkyl tartrate, dibutyl adipate, dicaprylyl carbonate, dicaprylyl ether, hexyl decanol, hydrogenated polyisobutene, isoeicosane, isohexadecane, isopropyl palmitate, isopropyl stearate, octyl cocoate, octyl isostearate, octyl octanoate, octyl palmitate, octyl stearate, octyl dodecanol, octyldodecyl myristate, isopropyl stearate, pentaerythrityl tetraisostearate, phenyl trimethicone, polydecene, propylene glycol dicaprylate/dicaprate, stearyl heptanoate, tricaprylin, tridecyl stearate, tridecyl trimellitate, triisostearin, or combinations thereof;

(c) about 30 to about 80 wt. %, more preferably about 35 to about 75 wt. %, even more preferably about 40 to about 60 wt. % of water;

(d) about 0.1 to about 40 wt. %, preferably about 1 to about 30 wt. %, more preferably about 5 to about 20 wt. % of one or more water soluble solvents, preferably wherein the one or more water soluble solvents, if present, is selected from mono-alcohols (for example $C_{2-8}$, or $C_{2-4}$ alcohols), polyols (polyhydric alcohols), glycols, and a mixture thereof, preferably wherein the water soluble solvent is glycerin or includes glycerin;

(f) about 0.01 to about 10 wt. %, preferably about 0.1 to about 6 wt. %, more preferably about 1 to about 5 wt. % of one or more electrolytes, preferably wherein the one or more electrolytes are selected from inorganic salts, more preferably wherein the one or more electrolytes are selected from sodium chloride, ammonium chloride, magnesium chloride, sodium sulfate, sodium citrate, or combinations thereof;

(g) optionally, one or more miscellaneous ingredients, preferably wherein the one or more miscellaneous ingredients, if present, are selected from preservatives, fragrances, pH adjusters, salts, chelating agents, buffers, antioxidants, flavonoids, vitamins, botanical extracts, UV filtering agents, proteins, protein hydrolysates, and/or isolates, fillers (e.g., organic and/or inorganic fillers such as talc, calcium carbonate, silica, etc.) composition colorants, wherein if present, are preferably in an amount of about 0.1 to about 15 wt. %, more preferably about 0.5 to about 10 wt. %, more preferably about 1 to about 6 wt. %;

wherein all percentages by weight are based on the total weight of the multiphase emulsion.

The multiphase cleansing composition typically phase separates shortly after the multiple phases are mixed, for example, by shaking. The multiphase cleansing composition may phase separate forming two distinct phases with a single interface within 15 minutes after shaking at about 25° C. In further embodiments, the multiphase cleansing composition will visibly phase separate into two or more layers within about 1 hour, about 30 minutes, about 15 minutes, about 10 minutes, about 8 minutes, about 5 minutes, about 2 minutes, or about 1 minutes at rest at 25° C. after shaking by hand.

In another preferred embodiment, the multiphase cleansing compositions comprise, consist of, or consist essentially of:

(i) about 10 to about 75 wt. %, preferably about 15 to about 50 wt. %, more preferably about 20 to about 40 wt. % of an oil phase comprising, consisting essentially of, or consisting of:

(a) about 0.01 to about 5 wt. %, preferably about 0.01 to about 3 wt. %, more preferably about 0.02 to about 3 wt. % of a hydrophobic polymer, which is a reaction product of a natural or food-derived oil and a methacrylate or acrylate polymer, wherein preferably, the hydrophobic polymer is a reaction product of: (a)(i) a natural or food-derived oil selected from linseed oil, sunflower oil, tung oil, fish oil, cottonseed oil, soybean oil, or combinations thereof, preferably linseed oil; and (a)(ii) a polymer derived from monomers selected from isobutyl methacrylate, methyl methacrylate, ethyl methacrylate, n-butyl methacrylate, and combinations thereof, preferably isobutyl methacrylate polymer, wherein even more preferably, the hydrophobic polymer is the reaction product of linseed oil and poly(isobutyl methacrylate);

(b) about 5 to about 60 wt. %, preferably about 15 to about 50 wt. %, more preferably 20 to about 40 wt. % of one or more solvents capable of solubilizing the reaction product of (a), wherein preferably, the one or more solvents capable of solubilizing the reaction product of (a) have a dispersion component (D), a polar component (P), and a hydrogen bonding component (H), and a distance (Ra) of less than or equal to 13.4 $MPa^{0.5}$ per Hansen Solubility Parameters, wherein the distance (Ra) is defined by formula (I):

$$Ra = \sqrt{4(D - D_1)^2 + (P - P_1)^2 + (H - H_1)^2} \quad \text{(I)}$$

wherein $D_1$ is 16.8 $MPa^{0.5}$, $P_1$ is 4.8 $MPa^{0.5}$, and $H_1$ is 13.0 $MPa^{0.5}$, wherein more preferably, the one or more solvents capable of solubilizing the reaction product of (a) have a dispersion component (D), a polar component (P), and a hydrogen bonding component (H), and a distance (Ra) of less than or equal to 9.9 $MPa^{0.5}$ per Hansen Solubility Parameters, wherein the distance (Ra) is defined by formula (I):

$$Ra = \sqrt{4(D - D_1)^2 + (P - P_1)^2 + (H - H_1)^2} \quad \text{(I)}$$

wherein $D_1$ is 16.4 $MPa^{0.5}$, $P_1$ is 5.0 $MPa^{0.5}$, and $H_1$ is 11.7 $MPa^{0.5}$, wherein even more preferably, at least one of the one or more solvents capable of dissolving the hydrophobic polymer of (a) are selected from dioctylcyclohexane, mineral oil, isocetyl palmitate, isocetyl palmitate, cyclopentasiloxane, dicaprylyl carbonate, octyl isostearate, trimethylhexyl isononanoate, 2-ethylhexyl isononanoate, dicaprylyl ether, dihexyl carbonate, polydecene, octyl cocoate, isodecyl neopentanoate, isohexy decanoate, isodecyl octanoate, dihexyl ether, isododecane, isodecyl 3,5,5 trimethyl hexanoate, oleyl erucate, *Passiflora incarnata* oil, jojoba oil, octyl palmitate, macadamia nut oil, isopropyl stearate, rapeseed oil, hexyl decanol, isotridecyl 3,5,5 trimethylhexanonanoate, polycitronellol acetate, mixed decanoyl and octanoyl glycerides, 2-ethylhexanoic acid, 3,5,5 trimethyl ester, cetystearyl octanoate, dimethicone, isopropyl palmitate, octyldodecanol, dioctyl adipate, isopropyl myristate, octyl palmitate (2-ethylhexyl palmitate), octyldodeceyl myristate, butyl octanoic acid, isopropyl stearate, caprylic/capric triglycerides, isopropyl isostearate, Jojoba oil, cyclomethicone, groundnut oil, almond oil, sunflower oil, decyl oleate, avocado oil, olive oil, dibutyl adipate, castor oil, calendula oil, wheatgerm oil, decyl oleate, avocado oil, calendula oil, propylene glycol monoisostearate, cocoglycerides, butylene glycol caprylate/caprate, C12-15 alkyl benzoate, caprylic/capric diglyceryl succinate, caprylic/capric triglyceride, cetearyl isononanoate, cetearyl octanoate, cetyl dimethicone, coco-caprylate/caprate, cocoglycerides, Di-C12-13 alkyl tartrate, dibutyl adipate, dicaprylyl carbonate, dicaprylyl ether, hexyl decanol, hydrogenated polyisobutene, isoeicosane, isohexadecane, isopropyl palmitate, isopropyl stearate, octyl cocoate, octyl isostearate, octyl octanoate, octyl palmitate, octyl stearate, octyl dodecanol, octyldodecyl myristate, isopropyl stearate, pentaerythrityl tetraisostearate, phenyl trimethicone, polydecene, propylene glycol dicaprylate/dicaprate, stearyl heptanoate, tricaprylin, tridecyl stearate, tridecyl trimellitate, triisostearin, or combinations thereof;

(ii) about 25 to about 80 wt. %, preferably about 40 to about 75 wt. %, more preferably about 45 to about 70 an aqueous phase comprising, consisting essentially of, or consisting of:

(a) about 30 to about 78 wt. %, more preferably about 35 to about 70 wt. %, even more preferably about 40 to about 65 wt. % of water;

(b) about 0.1 to about 40 wt. %, preferably about 1 to about 30 wt. %, more preferably about 5 to about 20 wt. % of one or more water soluble solvents, preferably wherein the one or more water soluble solvents, if present, is selected from mono-alcohols (for example $C_{2-8}$, or $C_{2-4}$ alcohols), polyols (polyhydric alcohols), glycols, and a mixture thereof, preferably wherein the water soluble solvent is glycerin or includes glycerin;

(c) about 0.01 to about 10 wt. %, preferably about 0.1 to about 6 wt. %, more preferably about 1 to about 5 wt. % of one or more electrolytes, preferably wherein the one or more electrolytes are selected from inorganic salts, more preferably wherein the one or more electrolytes are selected from sodium chloride, ammonium chloride, magnesium chloride, sodium sulfate, sodium citrate, or combinations thereof;

(d) optionally, one or more miscellaneous ingredients, preferably wherein the one or more miscellaneous ingredients, if present, are selected from preservatives, fragrances, pH adjusters, salts, chelating agents, buffers, antioxidants, flavonoids, vitamins, botanical extracts, UV filtering agents, proteins, protein hydrolysates, and/or isolates, fillers (e.g., organic and/or inorganic fillers such as talc, calcium carbonate, silica, etc.) composition colorants, wherein if present, are preferably in an amount of about 0.1 to about 15 wt. %, more preferably about 0.5 to about 10 wt. %, more preferably about 1 to about 6 wt. %;

wherein all percentages by weight are based on the total weight of the multiphase emulsion.

The multiphase cleansing composition typically phase separates shortly after the multiple phases are mixed, for example, by shaking. The multiphase cleansing composition may phase separate forming two distinct phases with a single interface within 15 minutes after shaking at about 25° C. In further embodiments, the multiphase cleansing composition will visibly phase separate into two or more layers within about 1 hour, about 30 minutes, about 15 minutes, about 10 minutes, about 8 minutes, about 5 minutes, about 2 minutes, or about 1 minutes at rest at 25° C. after shaking by hand.

In another preferred embodiment, the multiphase cleansing compositions comprise, consist of, or consist essentially of:

(i) about 10 to about 75 wt. %, preferably about 15 to about 50 wt. %, more preferably about 20 to about 40 wt. % of an oil phase comprising, consisting essentially of, or consisting of:

(a) about 0.01 to about 5 wt. %, preferably about 0.01 to about 3 wt. %, more preferably about 0.02 to about 3 wt. % of a hydrophobic polymer, wherein the hydrophobic polymer is a reaction product of linseed oil and poly(isobutyl methacrylate);

(b) about 5 to about 60 wt. %, preferably about 15 to about 50 wt. %, more preferably 20 to about 40 wt. % of one or more solvents capable of solubilizing the reaction product of (a), wherein preferably, the one or more solvents capable of solubilizing the reaction product of (a) have a dispersion component (D), a polar component (P), and a hydrogen bonding component (H), and a distance (Ra) of less than or equal to 9.9 $MPa^{0.5}$ per Hansen Solubility Parameters, wherein the distance (Ra) is defined by formula (I):

$$Ra = \sqrt{4(D - D_1)^2 + (P - P_1)^2 + (H - H_1)^2} \quad (I)$$

wherein $D_1$ is 16.4 $MPa^{0.5}$, $P_1$ is 5.0 $MPa^{0.5}$, and $H_1$ is 11.7 $MPa^{0.5}$, wherein even more preferably, at least one of the one or more solvents capable of dissolving the hydrophobic polymer of (a) are selected from dioctylcyclohexane, mineral oil, isocetyl palmitate, isocetyl palmitate, cyclopentasiloxane, dicaprylyl carbonate, octyl isostearate, trimethylhexyl isononanoate, 2-ethylhexyl isononanoate, dicaprylyl ether, dihexyl carbonate, polydecene, octyl cocoate, isodecyl neopentanoate, isohexy decanoate, isodecyl octanoate, dihexyl ether, isododecane, isodecyl 3,5,5 trimethyl hexanoate, oleyl erucate, *Passiflora incarnata* oil, jojoba oil, octyl palmitate, macadamia nut oil, isopropyl stearate, rapeseed oil, hexyl decanol, isotridecyl 3,5,5 trimethylhexanonanoate, polycitronellol acetate, mixed decanoyl and octanoyl glycerides, 2-ethylhexanoic acid, 3,5,5 trimethyl ester, cetystearyl octanoate, dimethicone, isopropyl palmitate, octyldodecanol, dioctyl adipate, isopropyl myristate, octyl palmitate (2-ethylhexyl palmitate), octyldodeceyl myristate, butyl octanoic acid, isopropyl stearate, caprylic/capric triglycerides, isopropyl isostearate, Jojoba oil, cyclomethicone, groundnut oil, almond oil, sunflower oil, decyl oleate, avocado oil, olive oil, dibutyl adipate, castor oil, calendula oil, wheatgerm oil, decyl oleate, avocado oil, calendula oil, propylene glycol monoisostearate, cocoglycerides, butylene glycol caprylate/caprate, C12-15 alkyl benzoate, caprylic/capric diglyceryl succinate, caprylic/capric triglyceride, cetearyl isononanoate, cetearyl octanoate, cetyl dimethicone, coco-caprylate/caprate, cocoglycerides, Di-C12-13 alkyl tartrate, dibutyl adipate, dicaprylyl carbonate, dicaprylyl ether, hexyl decanol, hydrogenated polyisobutene, isoeicosane, isohexadecane, isopropyl palmitate, isopropyl stearate, octyl cocoate, octyl isostearate, octyl octanoate, octyl palmitate, octyl stearate, octyl dodecanol, octyldodecyl myristate, isopropyl stearate, pentaerythrityl tetraisostearate, phenyl trimethicone, polydecene, propylene glycol dicaprylate/dicaprate, stearyl heptanoate, tricaprylin, tridecyl stearate, tridecyl trimellitate, triisostearin, or combinations thereof;

(ii) about 25 to about 80 wt. %, preferably about 40 to about 75 wt. %, more preferably about 45 to about 70 an aqueous phase comprising, consisting essentially of, or consisting of:

(a) about 30 to about 80 wt. %, more preferably about 35 to about 75 wt. %, even more preferably about 40 to about 60 wt. % of water;

(b) about 0.1 to about 40 wt. %, preferably about 1 to about 30 wt. %, more preferably about 5 to about 20 wt. % of one or more water soluble solvents, preferably wherein the one or more water soluble solvents, if present, is selected from mono-alcohols (for example $C_{2-8}$, or $C_{2-4}$ alcohols), polyols (polyhydric alcohols), glycols, and a mixture thereof, preferably wherein the water soluble solvent is glycerin or includes glycerin;

(c) about 0.01 to about 10 wt. %, preferably about 0.1 to about 6 wt. %, more preferably about 1 to about 5 wt. % of one or more electrolytes, preferably wherein the one or more electrolytes are selected from inorganic salts, more preferably wherein the one or more electrolytes are selected from sodium chloride, ammonium chloride, magnesium chloride, sodium sulfate, sodium citrate, or combinations thereof;

(d) optionally, one or more surfactants, wherein preferably the one or more surfactants are selected from anionic surfactants, nonionic surfactants, amphoteric surfactants, cationic surfactants, or combinations thereof, wherein more preferably, one or more anionic surfactants, one or more nonionic surfactants, one or more amphoteric surfactants, or combinations thereof, wherein more preferably one or more anionic surfactants selected from alkyl sulfonates, alkyl sulfosuccinates, alkyl sulfoacetates, acyl isethionates, alkoxylated monoacids, acyl amino acids such as acyl taurates, acyl glycinates, acyl glutamates, acyl sarcosinates, salts thereof, or mixtures thereof; and (e) optionally, one or more miscellaneous ingredients, preferably wherein the one or more miscellaneous ingredients, if present, are selected from preservatives, fragrances, pH adjusters, salts, chelating agents, buffers, antioxidants, flavonoids, vitamins, botanical extracts, UV filtering agents, proteins, protein hydrolysates, and/or isolates, fillers (e.g., organic and/or inorganic fillers such as talc, calcium carbonate, silica, etc.) composition colorants, wherein if present, are the one or more miscellaneous ingredients is preferably in an amount of about 0.1 to about 15 wt. %, more preferably about 0.5 to about 10 wt. %, more preferably about 1 to about 6 wt. %;

wherein all percentages by weight are based on the total weight of the multiphase emulsion.

The multiphase cleansing composition typically phase separates shortly after the multiple phases are mixed, for example, by shaking. The multiphase cleansing composition may phase separate forming two distinct phases with a single interface within 15 minutes after shaking at about 25° C. In further embodiments, the multiphase cleansing composition will visibly phase separate into two or more layers within about 1 hour, about 30 minutes, about 15 minutes, about 10 minutes, about 8 minutes, about 5 minutes, about 2 minutes, or about 1 minutes at rest at 25° C. after shaking by hand.

In another preferred embodiment, the multiphase cleansing compositions comprise, consist of, or consist essentially of:

(i) about 10 to about 75 wt. %, preferably about 15 to about 50 wt. %, more preferably about 20 to about 40 wt. % of an oil phase comprising, consisting essentially of, or consisting of:

(a) about 0.01 to about 5 wt. %, preferably about 0.01 to about 3 wt. %, more preferably about 0.02 to about 3 wt. % of a hydrophobic polymer, wherein the hydrophobic polymer is a reaction product of linseed oil and poly(isobutyl methacrylate);

(b) about 5 to about 60 wt. %, preferably about 15 to about 50 wt. %, more preferably 20 to about 40 wt. % of one or more solvents capable of solubilizing the reaction product of (a), wherein preferably the one or more solvents comprises or consists of caprylic/capric triglyceride, isopropyl myristate, isododecane, or mixtures thereof, (ii) about 25 to about 80 wt. %, preferably about 40 to about 75 wt. %, more preferably about 45 to about 70 an aqueous phase comprising, consisting essentially of, or consisting of:

(a) about 30 to about 80 wt. %, more preferably about 35 to about 75 wt. %, even more preferably about 40 to about 60 wt. % of water;

(b) about 0.1 to about 40 wt. %, preferably about 1 to about 30 wt. %, more preferably about 5 to about 20 wt. % of one or more water soluble solvents, preferably wherein the one or more water soluble solvents, if present, is selected from mono-alcohols (for example $C_{2-8}$, or $C_{2-4}$ alcohols), polyols (polyhydric alcohols), glycols, and a mixture thereof, preferably wherein the water soluble solvent is glycerin or includes glycerin;

(c) about 0.01 to about 10 wt. %, preferably about 0.1 to about 6 wt. %, more preferably about 1 to about 5 wt. % of one or more electrolytes, preferably wherein the one or more electrolytes are selected from inorganic salts, more preferably wherein the one or more electrolytes are selected from sodium chloride, ammonium chloride, magnesium chloride, sodium sulfate, sodium citrate, or combinations thereof;

(d) optionally, one or more surfactants, wherein preferably the one or more surfactants are selected from anionic surfactants, nonionic surfactants, amphoteric surfactants, cationic surfactants, or combinations thereof, wherein more preferably, one or more anionic surfactants, one or more nonionic surfactants, one or more amphoteric surfactants, or combinations thereof, wherein more preferably one or more anionic surfactants selected from alkyl sulfonates, alkyl sulfosuccinates, alkyl sulfoacetates, acyl isethionates, alkoxylated monoacids, acyl amino acids such as acyl taurates, acyl glycinates, acyl glutamates, acyl sarcosinates, salts thereof, or mixtures thereof; and (e) optionally, one or more miscellaneous ingredients, preferably wherein the one or more miscellaneous ingredients, if present, are selected from preservatives, fragrances, pH adjusters, salts, chelating agents, buffers, antioxidants, flavonoids, vitamins, botanical extracts, UV filtering agents, proteins, protein hydrolysates, and/or isolates, fillers (e.g., organic and/or inorganic fillers such as talc, calcium carbonate, silica, etc.) composition colorants, wherein if present, are the one or more miscellaneous ingredients is preferably in an amount of about 0.1 to about 15 wt. %, more preferably about 0.5 to about 10 wt. %, more preferably about 1 to about 6 wt. %;

wherein all percentages by weight are based on the total weight of the multiphase emulsion.

The multiphase cleansing composition typically phase separates shortly after the multiple phases are mixed, for example, by shaking. The multiphase cleansing composition may phase separate forming two distinct phases with a single interface within 15 minutes after shaking at about 25° C. In further embodiments, the multiphase cleansing composition will visibly phase separate into two or more layers within about 1 hour, about 30 minutes, about 15 minutes, about 10 minutes, about 8 minutes, about 5 minutes, about 2 minutes, or about 1 minutes at rest at 25° C. after shaking by hand.

EXAMPLES

Implementation of the present disclosure is provided by way of the following examples. The examples serve to illustrate the technology without being limiting in nature.

Example 1

Compositions

Inventive compositions A-C and Comparative Composition D were prepared as described below and a Commercial Benchmark Multiphase Cleansing composition (E) was obtained.

| | | | Inventive | | | Comp. | Bench. |
|---|---|---|---|---|---|---|---|
| | | | A | B | C | D | E |
| Oil | (a) | MYCELX ®[1] | 0.02 | 0.05 | 0.09 | 0 | 0 |
| Phase | (b) | CAPRYLIC/CAPRIC TRIGLYCERIDE | 4 | 4 | 4 | 4 | * |
| | | ISOPROPYL MYRISTATE | 18 | 18 | 18 | 18 | |
| | | ISODODECANE | 9 | 9 | 9 | 9 | |
| Water | (c) | WATER | 54 | 54 | 54 | 54 | |
| Phase | (d) | GLYCERIN | 12 | 12 | 12 | 13 | |
| | (e) | NaCl | 3 | 3 | 3 | 3 | |
| Speed of separation in Seconds (appearance of interface) | | | 61 | 32 | 25 | >2000 >33 min. | >1000 >16 min. |
| Oil Phase Translucent/Transparent | | | Yes | Yes | Yes | No | Yes |
| Water Phase Transparency | | | Yes | Yes | Yes | Yes | Yes |

[1]Reaction product of linseed oil and isobutyl methacrylate polymer

* The commercial benchmark product reports the following ingredients list:

Water, Cyclopentasiloxane, Isohexadecane, Sodium Chloride, Poloxamer 184, Hexylene Glycol, Dipotassium Phosphate, Benzyl Alcohol, Potassium Phosphate, Quaternium-15, Benzalkonium Chloride, Parfum/Fragrance, Citronellol, Geraniol.

The compositions, except for the commercial benchmark product (E), were prepared by combining the water, glycerin, and salt to form an aqueous phase. Separately, the Mycelx®, the caprylic/capric triglyceride, and isopropyl myristate were combined to form a first oil phase. MycelX® dissolves in the first oil phase. The first oil phase is then combined with isododecane to form a second oil phase. MycelX® has poor solubility in isododecane alone (<5%) but when combined in a first oil phase and subsequently combined with the isododecane, the MycelX® remains solubilized in the second oil phase. The second oil phase and the aqueous phase are then combined to form final compositions.

Figure 1B:
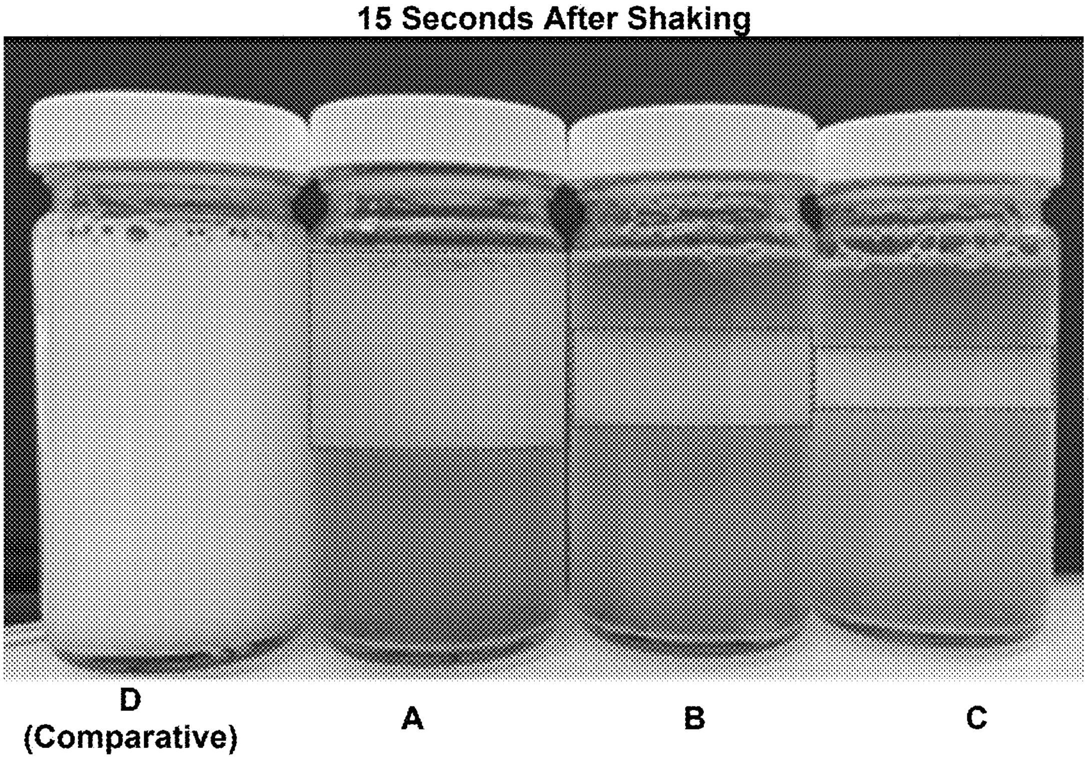
Figure 1C:
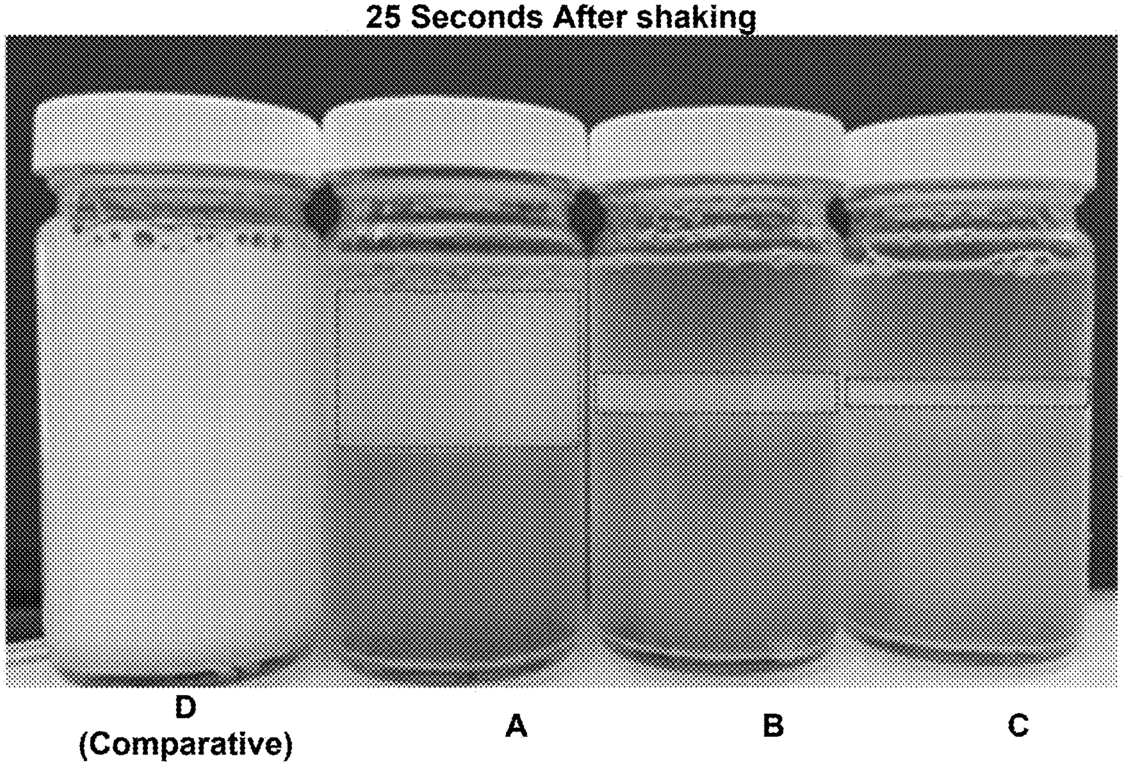

The final compositions were transferred to transparent bottles for observation. The bottles were vigorously shaken for 10 seconds to form temporary emulsions having an opaque appearance. After shaking, the compositions were monitored to determine how quickly they phase separated and formed a thin interface boarder between the aqueous phases and the oil phase. The time to phase separation (time to formation of an interface) is reported in the table above. Pictures of the compositions and the progression to phase separation is shown in FIG. 1(*a*) (immediately after shaking), FIG. 1(*b*) (15 seconds after shaking), and FIG. 1(*c*) (25 seconds after shaking).

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting. Appropriate counterions for the components described herein are known in the art.

The expression "one or more" means "at least one" and thus includes individual components as well as mixtures/combinations.

The term "plurality" means "more than one" or "two or more."

The term "transparent" with respect to a transparent composition indicates that the composition has transmittance of at least 80% at a wavelength of 600 nm, for example measured using a Lambda 40 UV-visible spectrometer. The compositions may have, for example, a transmittance of at least 80%, at least 90%, or at least 95% at a wavelength of 600 nm, measured, for example, using a Lambda 40 UV-visible spectrometer. The term "clear" is interchangeable with the term "transparent" for purposes of the instant disclosure.

The term "translucent" with respect to a translucent composition indicates that the composition has a transmittance of at least 50% at a wavelength of 600 nm, for example measured using a Lambda 40 UV-visible spectrometer.

Other than in the operating examples, or where otherwise indicated, all amount expressing quantities of ingredients and/or reaction conditions may be modified in all instances by the term "about," meaning within +/−5% of the indicated number. Thus, for a range of "about 1 to about 10 wt. %," The lower amount of "about 1 wt. %" may extend down to 0.95 wt. %, which is 5% less than 1 wt. %. The higher amount of "about 10 wt. %" may extend up to 10.5 wt. %, which is 5% higher than 10 wt. %, i.e., a range of "0.95 wt. % to 10.5 wt. %."

All percentages, parts and ratios herein are based upon the total weight of the compositions of the present invention, unless otherwise indicated.

Some of the various categories of components identified may overlap. In such cases where overlap may exist and the composition includes both components (or the composition includes more than two components that overlap), an overlapping compound does not represent more than one component. For example, certain compounds may be considered both oily solvent and a surfactant. If a particular composition includes both an oily solvent and a surfactant, a single compound will serve as only the oily solvent or only as the surfactant (the single compound does not simultaneously serve as both the oily solvent and the surfactant).

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. For example, if a composition is essentially free from compound X, the composition includes less that 2 wt. % of compound X, or less than 1 wt. % of compound X, or less than 0.5 wt. % of compound X, or less than 0.1 wt. % of compound X, or is free from compound X.

All components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference in their entirety, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A multiphase cleansing composition comprising:
(i) an oil phase comprising:
(a) a hydrophobic polymer formed by reacting about 72 to about 77 parts by weight of a natural or food-derived oil and about 23 to about 28 parts by weight of a methacrylate or acrylate polymer;
(b) one or more solvents capable of solubilizing the hydrophobic polymer;
(ii) an aqueous phase comprising:
(a) water.

2. The composition of claim 1, wherein the hydrophobic polymer is formed by reacting the natural or food-derived oil and the methacrylate polymer.

3. The composition of claim 1, wherein the natural or food-derived oil is a drying oil or semi-drying oil selected from linseed oil, sunflower oil, tung oil, fish oil, cottonseed oil, soybean oil, or combinations thereof.

4. The composition of claim 1, wherein the methacrylate or acrylate polymer is derived from monomers selected from isobutyl methacrylate, methyl methacrylate, ethyl methacrylate, n-butyl methacrylate, or combinations thereof.

5. The composition of claim 1, wherein the methacrylate or acrylate polymer is poly(isobutyl methacrylate).

6. The composition of claim 1, wherein the hydrophobic polymer is formed by reacting linseed oil and poly(isobutyl methacrylate).

7. The composition of claim 1, wherein the one or more solvents capable of solubilizing the hydrophobic polymer have a dispersion component (D), a polar component (P), a hydrogen bonding component (H), and a distance (Ra) of less than or equal to 13.4 $MPa^{0.5}$ as per Hansen Solubility Parameters, wherein the distance (Ra) is defined by formula (I):

$$Ra = \sqrt{4(D - D_1)^2 + (P - P_1)^2 + (H - H_1)^2} \quad \text{(I)}$$

wherein
$D_1$ is 16.8 $MPa^{0.5}$,
$P_1$ is 4.8 $MPa^{0.5}$, and
$H_1$ is 13.0 $MPa^{0.5}$.

8. The composition of claim 1, wherein at least one of the one or more solvents capable of solubilizing the hydrophobic polymer is selected from polycitronellol acetate, caprylic/capric triglyceride, isododecane, isohexadecane, tetradecane, isopropyl myristate, isopropyl alcohol, octyldodecanol, ethanol, phenoxyethanol, castor oil, or combinations thereof.

9. The composition of claim 1, further comprising one or more water-soluble solvents.

10. The composition of claim 9, wherein the one or more water-soluble solvents are selected from $C_2$-$C_6$ mono-alcohols, polyols, glycols, and combinations thereof.

11. The composition of claim 1, further comprising one or more electrolytes.

12. The composition of claim 11, wherein the one or more electrolytes are selected from sodium chloride, ammonium chloride, magnesium chloride, sodium sulfate, sodium citrate, or combinations thereof.

13. The composition of claim 1, wherein the composition is free or essentially free from emulsifiers and surfactants.

14. The composition of claim 1, wherein the composition phase separates within about 5 minutes at 25° C. after shaking.

15. A multiphase cleansing comprising:
(i) about 20 to about 50 wt. % of an oil phase comprising:
(a) about 0.01 to about 2 wt. % of a hydrophobic polymer formed by reacting about 72 to about 77 parts by weight of linseed oil and about 23 to about 28 parts by weight of isobutyl methacrylate polymer;
(b) about 5 to about 50 wt. % of one or more solvents capable of solubilizing the hydrophobic polymer having a dispersion component (D), a polar component (P), and a hydrogen bonding component (H), and a distance (Ra) per Hansen Solubility Parameters of less than or equal to 13.4 $MPa^{0.5}$, wherein the distance (Ra) is defined by formula (I):

$$Ra = \sqrt{4(D - D_1)^2 + (P - P_1)^2 + (H - H_1)^2} \quad \text{(I)}$$

wherein
$D_1$ is 16.8 $MPa^{0.5}$,
$P_1$ is 4.8 $MPa^{0.5}$, and
$H_1$ is 13.0 $MPa^{0.5}$;

(ii) about 40 to about 80 wt. % of an aqueous phase comprising:
(a) about 30 to about 99 wt. % of water;
(b) about 0.01 to about 20 wt. % of one or more water soluble solvents;
(c) optionally, one or more electrolytes;

wherein all weight percentages are based on a total weight of the multiphase cleansing composition, and the multiphase cleansing composition phase separates within about 5 minutes at 25° C. after shaking.

16. A method for cleansing skin or hair comprising:

(a) shaking or mixing the multiphase cleansing composition of claim 1 to form a mixed application composition;

(b) applying the mixed application composition to the skin or hair;

(c) removing the mixed application composition from the skin or hair, wherein removing the mixed application composition optionally comprises rinsing the skin or hair with water.

17. A method for removing makeup from skin or hair comprising:

(a) shaking or mixing the multiphase cleansing composition of claim 1 to form a mixed application composition;

(b) applying the mixed application composition to skin or hair upon which makeup is present;

(c) removing the mixed application composition from the skin or hair, wherein removing the mixed application composition optionally comprises rinsing the skin or hair with water.

* * * * *